(12) United States Patent
Kurschel

(10) Patent No.: US 12,161,828 B2
(45) Date of Patent: Dec. 10, 2024

(54) ATTACHMENT FOR A DEVICE FOR GENERATING AN AIR FLOW OR DISPENSING A FLUID INTO THE EXTERNAL AUDITORY CANAL

(71) Applicant: Earbreeze GmbH, Wein (AT)

(72) Inventor: Martin Kurschel, Vienna (AT)

(73) Assignee: Earbreeze GmbH, Wein (AT)

( * ) Notice: Subject to any disclaimer, the term of this patent is extended or adjusted under 35 U.S.C. 154(b) by 343 days.

(21) Appl. No.: 17/808,426

(22) Filed: Jun. 23, 2022

(65) Prior Publication Data

US 2022/0323668 A1   Oct. 13, 2022

Related U.S. Application Data

(63) Continuation of application No. 17/259,980, filed as application No. PCT/EP2019/068915 on Jul. 13, 2019, now Pat. No. 11,413,390.

(30) Foreign Application Priority Data

Jul. 13, 2018   (EP) ..................... 18183454

(51) Int. Cl.
*A61F 11/08*   (2006.01)
*A61F 7/12*   (2006.01)
(Continued)

(52) U.S. Cl.
CPC ............. *A61M 3/0279* (2013.01); *A61F 7/12* (2013.01); *A61F 11/08* (2013.01); *A61F 2007/0005* (2013.01); *A61F 2007/0059* (2013.01); *A61F 2007/0069* (2013.01); *A61F 2007/0087* (2013.01); *A61F 11/085* (2022.01); *A61M 2206/16* (2013.01); *A61M 2210/0662* (2013.01); *F26B 9/003* (2013.01)

(58) Field of Classification Search
CPC .... A61F 11/00; A61F 7/12; A61F 2007/0005; A61F 11/006; A61M 3/0279
See application file for complete search history.

(56) References Cited

U.S. PATENT DOCUMENTS 5,364,343 A   11/1994   Apolet et al.
6,210,358 B1   4/2001   Roger
(Continued)

FOREIGN PATENT DOCUMENTS

CN   1295826 A   5/2001
CN   104797220 A   7/2015
(Continued)

OTHER PUBLICATIONS

Extended European Search Report; Application No. 18183454.0; Completed: Dec. 20, 2018; Mailing Date: Jan. 7, 2019; 7 Pages.
(Continued)

*Primary Examiner* — Deanna K Hall
(74) *Attorney, Agent, or Firm* — Husch Blackwell LLP

(57) ABSTRACT

An attachment for a device for generating an air flow or dispensing a fluid, which attachment is designed to be at least partially introduced into an external auditory canal of a human or animal ear, the attachment including a connection piece for connecting the attachment to the device for generating an air flow, and a tongue-type guide vane for conducting air that flows out of the device for generating an air flow via the connection piece, the guide vane having a bottom.

30 Claims, 11 Drawing Sheets

(51) Int. Cl.
  *A61M 3/02* (2006.01)
  *A61F 7/00* (2006.01)
  *F26B 9/00* (2006.01)

(56) References Cited

U.S. PATENT DOCUMENTS

| | | |
|---|---|---|
| 2004/0060192 A1 | 4/2004 | Gronka |
| 2009/0041279 A1 | 2/2009 | Davis |
| 2011/0099832 A1 | 5/2011 | Bikhazi |
| 2015/0090191 A1 | 4/2015 | Kokenis |
| 2018/0125345 A1 | 5/2018 | Rebella et al. |

FOREIGN PATENT DOCUMENTS

| | | |
|---|---|---|
| DE | 69214690 T2 | 11/1996 |
| EP | 0243261 A1 | 10/1987 |
| EP | 0266383 A1 | 5/1988 |
| EP | 0937422 B1 | 5/2003 |
| WO | 0010627 A1 | 3/2000 |
| WO | 2012166801 A1 | 12/2012 |

OTHER PUBLICATIONS

International Preliminary Report on Patentability; Application No. PCT/EP2019/068915; Issued: Sep. 30, 2020; 29 Pages.
International Search Report and Written Opinion of the International Searching Authority with Translation; Application No. PCT/EP2019/068915; Completed: Sep. 6, 2019; Issued: Sep. 20, 2019; 10 Pages.
Chinese Office Action; Application No. 201980052466.7; Dated: Sep. 22, 2021; 12 Pages.
United States Office Action; U.S. Appl. No. 16/293,215; Issued: May 17, 2021; 15 Pages.
United States Office Action; U.S. Appl. No. 16/293,215; Issued: Oct. 20, 2021; 6 Pages.

ATTACHMENT FOR A DEVICE FOR GENERATING AN AIR FLOW OR DISPENSING A FLUID INTO THE EXTERNAL AUDITORY CANAL

TECHNICAL FIELD

The present teaching relates to an attachment for a device for generating an air flow, preferably a warm air flow, or for dispensing a fluid, which attachment is designed to be at least partially introduced into an external auditory canal of a human or animal ear in order to dry up accumulations of moisture in the external auditory canal. In addition, the present teaching relates to an ear-drying tool comprising a device for generating an air flow as well as the inventive attachment. The present teaching further relates to a tool for care or therapeutic treatment of the external auditory canal of a human or animal ear.

BACKGROUND

Patients suffering from chronic moist auditory canals—whether because of a radical cavity, an eardrum wall perforation or another disorder of the external auditory canal—or wearers of hearing aids are frequently confronted with the problem of efficient removal of moisture from the external auditory canal of the ear. In addition, water can enter the auditory canal while a person is in the bathtub, taking a shower or swimming, leading to reduced hearing acuity. Moreover, bacteria, germs and impurities can thereby more easily reach the external auditory canal, causing inflammations there and requiring rapid removal of these liquid accumulations.

From the prior art, however, no devices are known that can help make such removal possible in a safe and efficient way. For example, it is a familiar practice to introduce an air flow into the auditory canal, by which the external auditory canal is to be dried. An attachment that can be inserted into the external auditory canal for generating an air flow is known, for example, from patent EP 0937422 B1. First of all, however, the attachment proposed therein conducts the air inserted into the external auditory canal directly to the eardrum wall of the treated ear, possibly causing injuries and residual harm; in addition, because of its structure the attachment can be inserted only to the depth of a few millimeters, or not at all, into the patient's auditory canal, and thereby, in particular, accumulations of moisture in the end region close to the eardrum of the normally 2 to 2.5 cm long auditory canal cannot be removed except possibly after lengthy application and/or greater intensity of the air flow.

Analogously, in freeing the external auditory canal of cerumen by means of a fluid, injuries of the eardrum can result if the fluid is applied directly to the eardrum. At the same time, cerumen deposits can remain in the external auditory canal, and thus cleaning of the external auditory canal may be unsatisfactory if fluid cannot reach the entire external auditory canal. Devices for cleaning the external auditory canal are known, for example, from EP 0 243 261 A1 and DE 692 14 690 T2.

Also, in the context of conducting a fluid into the external auditory canal for the purpose of care or therapeutic treatment of the external auditory canal, injuries of the eardrum can occur if the fluid is applied directly to the eardrum. The cleansing or therapeutic effect of such a treatment of the external auditory canal by means of a fluid, in addition, can fail to achieve its maximum effect if the fluid cannot penetrate the entire external auditory canal.

SUMMARY

It is accordingly one object of the present teaching to provide an attachment for a device for generating an air flow, preferably a warm air flow, which attachment makes possible the rapid and efficient removal of moisture from the external auditory canal of a human or an animal by means of an air flow, without thereby exposing the eardrum wall to the risk of injury.

In addition, the provided attachment is intended to be adaptable to different auditory canals in a non-complex manner, to comprise a simple structure and to be cost-effective in production.

The efficiency of ear-drying instruments that include the inventive attachment, moreover, should be significantly increased. The inventive ear-drying instrument is to provide a marked drying outcome after as little as 15 seconds' application duration. It should be possible to achieve complete drying after an application duration of no more than 30 seconds.

In addition, it is an object of the present teaching to provide an attachment for a device for generating a fluid, which attachment makes possible the rapid and efficient removal of cerumen from the external auditory canal of a human or animal by means of a fluid, without at the same time exposing the eardrum to the risk of injury.

Finally, it is an object of the present teaching to provide an attachment for a device for generating a fluid, which attachment makes possible the rapid and efficient care or therapeutic treatment of the external auditory canal of a human or animal by means of a fluid, without at the same time exposing the eardrum to the risk of injury.

One object of the present teaching is fulfilled, according to the present teaching, by an attachment for a device for generating an air flow, preferably a warm air flow, or for releasing a fluid, which attachment is designed to be at least partially introduced into an external auditory canal of a human or animal ear, wherein the attachment comprises a connection piece for connection to the device for generating an air flow, and a tongue-type guide vane, standing apart from the connection piece, with a guide vane bottom for conducting air that flows out of the device or fluid that is dispensed from said device, and wherein the guide pane is mounted behind the connection piece in the streaming direction of the air flow or fluid, wherein the guide vane bottom of a first portion of the guide vane having a lengthwise-section course, which is curved in a first direction, and the guide vane bottom of a second portion of the guide vane has a lengthwise-section course, which is curved in a second direction, and both curved portions run in a curve in directions opposite one another. The connection piece here can be of various configurations. It can, for instance, constitute an essential element of the attachment and provide the latter with stability. Or else it can merely form a portion of the attachment, which serves to connect the attachment to the device without at the same time contributing to the stability of the attachment.

According to the present teaching, the air flow provided by the device is introduced into the external auditory canal by the inventive attachment and then directed by the guide vane in such a way that, inside the external auditory canal, a stream develops that is particularly advantageous for the desired drying effect. The air flow thus streams by means of the connection piece into the attachment, flows first through the connection piece and is fed thereafter by the guide vane bottom of the guide vane in the direction of the external auditory canal. Thanks to the inventive course of the guide vane or the curvature of the guide vane bottom, an especially favorable stream distribution of the air flow is achieved inside the external auditory canal. Particularly in comparison with attachments whose guide vane bottom has a straight lengthwise-section course, especially good drying results were successfully achieved. It is particularly advantageous here if—viewed from the connection piece—the gradient of a tangent arranged to the guide vane bottom in the first portion of the guide vane bottom decreases with the distance from the connection piece and in the second portion of the guide vane bottom increases with the distance from the connection piece. The air flow is directed through the inventive attachment in such a way that something like an eddy is formed inside the external auditory canal. The said eddy—depending on how far the attachment is introduced into the external canal of the subject's auditory canal—can either occur because of a spin, which the air flow undergoes on account of the guide pane, and/or can be formed because of reflection of the air flow on lateral walls leading to the eardrum. The air flow, consequently, rather than strike directly against the eardrum, can instead be reflected only onto the lateral walls of the external auditory canal, preferably repeatedly, before it is conducted along the eardrum, so that it sweeps along the eardrum surface. For example, the air flow can strike against an upper lateral wall of the auditory canal, can be reflected there and can be conducted along the eardrum in the direction of a lower lateral wall of the external auditory canal, where the air flow is once again reflected and finally moved in the direction of the outer ear. It is also possible for the air flow to be reflected multiple times on the lateral walls of the external auditory canal before the air flow reaches the eardrum. In particular, by means of the inventive attachment, moisture accumulations can also be removed from the Recessus meatus acustici externi, that is, from that trough that is found directly in front of the eardrum between the floor of the external auditory canal running diagonally down onto the eardrum and the diagonally standing eardrum which canopies this floor. The turbulence of the air flow, whether it is from the twisting and/or from reflection on the lateral walls of the external auditory canal leading to the eardrum, has the result that the air flow sweeps over the eardrum and the Recessus meatus acustici externi, rather than colliding frontally against the eardrum. Because of the streaming pathway of the air flow inside the external auditory canal, determined by the inventive attachment, there only especially short application periods are necessary for satisfactory drying. For example, an appreciable drying effect can be obtained even after 15 seconds if an inventive ear-drying device—as described further hereinafter—is employed having the inventive attachment. To dry the external auditory canal—that is, to reduce the moisture content in the auditory canal back to the customary quantity—an application period of about 30 seconds or less is sufficient.

In addition, it has been shown that the inventive attachment also makes possible the especially protective and simultaneously effective removal of cerumen from the external auditory canal if the attachment is used in connection with a device for dispensing a fluid. On the basis of the inventive guide vane, the fluid, for instance water, forms inside the external auditory canal an especially favorable stream pathway for cleaning. Analogously to the air flow described above, the fluid is also forced into a quasi-eddy when it streams into the external auditory canal, so that, on the one hand, a direct strike of the fluid against the eardrum is prevented and, at the same time, thanks to the turbulence and/or reflection of the fluid on the lateral walls of the external auditory canal, especially effective removal of cerumen adhering to the lateral walls is ensured.

It has further been demonstrated that the inventive attachment also makes possible an especially protective and simultaneously effective care and therapeutic treatment of the external auditory canal if the attachment is used in connection with a device for dispensing a fluid. As a result of the inventive guide vane, the fluid inside the external auditory canal configures an especially favorable streaming pathway for care and therapeutic treatment of the external auditory canal. Injuries of the eardrum can be avoided here and maximization of the care or therapeutic effect can be achieved, because the fluid used for care or therapeutic treatment is not conveyed directly onto the eardrum and, because of the inventive turbulence and/or reflection of the fluid, can reach the lateral walls of the external auditory canal especially well.

According to a preferred embodiment of the present teaching, it can be foreseen that the first portion and the second portion are directly contiguous. In particular, it is favorable in streaming technology terms if the first portion and the second portion of the guide vane bottom are not severed from one another by any discontinuity but instead flow directly into one another.

This results in a streaming pathway of the air flow serving for drying inside the external auditory canal, which pathway is especially favorable for the desired drying effect.

To realize the inventive effect described above, which makes possible a protective drying of the eardrum, it is basically sufficient to introduce the tongue-shaped guide vane into the external auditory canal and exploits either the turbulence of the air flow caused by the guide vane or the reflection and/or turbulence likewise caused by the guide vane and/or turbulence on the walls of the external auditory canal; yet it can be advantageous, in addition, to employ an ear funnel as the attachment.

According to an additional preferred embodiment of the inventive attachment, it is therefore foreseen that the attachment should include an ear funnel, which surrounds the tongue-like guide vane at least partially, preferably entirely, in lengthwise direction and comprises a proximal opening, with which proximal opening the attachment, when appropriately used, is introduced into or applied to the external auditory canal, so that the proximal opening constitutes the closest opening of the ear funnel to the eardrum, wherein the ear funnel is connected to the connection piece and stands apart from it, or the connection piece configures an end portion of the ear funnel.

The ear funnel thus serves as that part of the attachment which is brought into direct contact with the external auditory canal or the lateral walls of the same when the attachment is used as intended and is introduced into the external auditory canal of the subject. The ear funnel can be connected with the connection piece of the attachment and can extend from it or the connection piece can form an end portion of the ear funnel. The guide vane is arranged at least partially inside the preferably sleeve-shaped ear tunnel. Preferably, the guide vane does not extend out of the ear funnel. The ear funnel makes possible, on the one hand, easy widening and advantageous positioning for drying—specifically, easy straightening—of the usually diagonally running external auditory canal if the attachment is introduced with the ear funnel into the external auditory canal of a person or animal; on the other hand, the ear funnel also allows easy adjustment of the attachment to the various conditions such as use in adults or children—such as by a corresponding choice of shape and size of the ear trumpet. The length of the ear funnel can be adjusted to the lengthwise course of the guide vane in order to support the formation of the turbulences and reflections described above in the external auditory canal. Upon intended use of the attachment for trying the external auditory canal, the attachment with the proximal opening of the ear funnel is introduced into the subject's external auditory canal or applied to it. The term "proximal" refers here and hereinafter to the position of a particular element with respect to the subject's eardrum. Concretely, the proximal opening means the opening of the ear funnel closest to the subject's eardrum.

With an additional preferred embodiment of the inventive attachment, it is foreseen that, from the viewpoint of a lengthwise section of the attachment, the guide vane bottom intersects a lengthwise axis of the attachment, which lengthwise axis runs through the center point of the portion of the connection piece standing perpendicular to the lengthwise portion.

The tongue-type guide vane of the attachment intersects the lengthwise axis running through the center point of the portion of the connection piece. According to the present teaching, this assumes that the guide vane in a lateral view of the attachment runs at least partially diagonally to this lengthwise axis. Preferably, the guide vane, viewed along its length in the streaming direction, can have a non-disappearing gradient. Because the guide vane, in particular the lengthwise portion of the guide vane bottom, diagonally intersects the lengthwise axis of the attachment, the air flow is guided in such a way that it does not directly strike against the subject's eardrum.

According to another preferred embodiment of the inventive attachment, it is foreseen that, in viewing a lengthwise section of the attachment, the guide vane bottom intersects a lengthwise axis of the ear funnel, which lengthwise axis runs through the centerpiece of the proximal opening of the ear funnel.

Provided that the ear funnel is rotation symmetrical—which is the case, apart from an outlet opening in the enclosure of the ear funnel—the lengthwise axis of the ear funnel coincides with its rotation axis. The guide vane can be arranged inside the ear funnel in such a way that, viewed in a lengthwise section, the guide vane bottom intersects the lengthwise axis of the ear funnel, wherein it has proved especially effective for the intended turbulences or reflections and thus for the desired drying, if the guide vane bottom intersects the lengthwise axis of the ear funnel in a proximal end portion of the ear funnel.

Preferably the lengthwise axis of the ear funnel coincides with the lengthwise axis of the attachment. Thereby the structure of the inventive attachment can be kept particularly simple.

According to an additional preferred embodiment of the inventive attachment, it is foreseen that the tongue-type guide vane comprises two guide vane frames extending from the guide vane bottom, namely a first guide vane frame and a second guide vane frame, wherein guide vane bottoms and guide vane frames configure a guide channel or part of a guide channel for the air flowing from the device for generating an air flow.

The guide vane frames make it possible to ensure targeted and controlled guidance of the air flow along the guide vane as well as controlled emission of the air flow to the external auditory canal. In addition, with embodiments of the attachment having an ear funnel, any undesired reflections of the air flow on an interior wall of the ear funnel can be avoided. Here the guide pane frames can be in contact with the ear funnel, for example, over the entire length of the guide pane bottom or else in one or more lengthwise sections of the guide pane bottom. Alternatively, the guide pane frames can also be placed at a distance from the ear funnel.

According to an additional preferred embodiment, it is foreseen that the first guide pane frame extends from a first lengthwise border of the guide pane bottom and the second guide pane frame extends from a second lengthwise border situated opposite the first lengthwise border. Alternatively, it can also be foreseen that the first guide pane frame is configured by the first lengthwise border of the guide pane bottom and the second guide pane frame by the second lengthwise border of the guide pane bottom.

Here the guide pane frames restrict the guide pane bottom to its lengthwise sides which are opposite one another and, to the greatest possible extent, make it impossible for the air flow from the guide channel serving for drying to reach other areas of the attachment, such as an exhaust air duct, before the said air flow arrives at the external auditory canal for the intended drying. If the guide pane frames, on the other hand, are in contact with the ear funnel along their entire length, such an overflow of air from the guide channel into other areas, such as the exhaust air duct, can be completely prevented, are isolated or separated in a fluid manner from one another. In this way, guide channel and exhaust air duct can be isolated or separated from one another in a fluid-like manner by the guide panel. Particularly advantageous drying effects can be achieved if the guide pane frames extend over the entire length of the guide panes. The guide pane frames can also be produced as a single unit with the guide pane bottoms and can be configured by the first lengthwise border and the second lengthwise border opposite to it. The guide pane frames can comprise a cross-section profile with a different curvature in comparison to the guide pane bottoms situated between the guide pane frames. The transition between the guide pane bottoms and the guide pane frames can be continuous, taking the form for instance of a change in the gradient or curvature of the cross-section profile of the guide pane bottom. This can make it difficult to distinguish unequivocally between guide pane bottom and guide pane frame. For example, guide pane bottom and guide pane frame can be arranged in such a way that an overall cross-section of the guide pane configured by guide pane bottom and guide pane frame is essentially U-shaped in configuration.

According to an additional preferred embodiment of the inventive attachment, it is foreseen that the tongue-type guide pane comprises a portion that runs in the connection piece.

This is particularly advantageous when the attachment comprises no ear funnel or a removable one. The connection piece in this case serves on the one hand for connection to the device, and on the other hand gives the attachment the required stability to support the guide pane.

To avoid injuries to the eardrum and/or to the lateral wall of the external auditory canal, in another preferred embodiment of the inventive attachment it is foreseen that the tongue-type guide pane is arranged completely inside the ear funnel and/or the connection piece.

With attachments according to this embodiment of the present teaching, risk of injuries to the subject's eardrum and/or the lateral walls of the external auditory canal can be minimized, because the entire guide pane is protected inside the attachment. In particular, the first and second portions of the guide pane can be mounted inside the ear funnel and the portion of the guide pane running in the connection piece.

According to an additional preferred embodiment of the attachment and according to this present teaching, it is foreseen that the ear funnel narrows from the connection piece all the way to the proximal opening of the ear funnel.

The proximal opening preferably has a circular circumference and a diameter of no more than 7 mm. Because the shape of the ear funnel thereby is adapted to the shape of the external auditory canal, at least in the proximal end region of the ear funnel, said end region being introduced into the auditory canal, this makes possible an especially simple and pain-free introduction of the attachment into the external auditory canal. The inventive attachment can thus be inserted far toward the subject's eardrum, such as up to 20 mm, preferably 15 mm, particularly preferably 10 mm, so that the configuration of the quasi-eddy in the external auditory canal, as described above, can be supported and the drying of liquid accumulations in the Recessus meatus acustici externi can be facilitated. The minimum achievable distance from the eardrum can vary, depending on the special suitability of the attachment for use in men, women or children.

It is particularly preferable if the proximal end of the guide pane, closest to the eardrum (31), preferably a proximal end of the guide pane bottom, is arranged inside the proximal opening of the ear funnel.

In such embodiments of the present teaching, the guide pane essentially ends flush with the ear funnel. This is especially favorable for guiding the air flow exiting from the attachment through the proximal opening of the ear funnel into the external auditory canal. Both an exit angle, at which the air flow—based on the lengthwise axis of the ear funnel or attachment—flows out of the attachment, and a swirling, which is to be applied to the air flow upon exiting from the attachment, can be developed especially well in this embodiment.

According to an additional preferred embodiment of the inventive attachment, it is foreseen that the proximal end of the guide pane, preferably a proximal end of the guide pane bottom, divides the proximal opening of the ear funnel into an outlet opening for air flowing out of the attachment into the auditory canal and an inflow opening for air flowing out of the auditory canal into the attachment.

Thus, on the one hand, the dry air flow serving for drying, preferably a warm air flow, streams through the proximal opening of the ear funnel out of the attachment into the external auditory canal—namely in the area of the outflow opening—and on the other hand, moist air can flow out of the external auditory canal through the proximal opening as well as back into the attachment—namely in the area of the inflow opening. Thus, the ear funnel also makes possible the outflow of the air serving for drying out of the auditory canal and prevents the formation of a congestion of the flow inside the auditory canal. Moist air can again leave the external auditory canal immediately after the absorption of moisture and isolated from the lateral walls of the external auditory canal, thus yielding an improved drying effect. It can thereby be ensured that the air flow used for drying in the area of the proximal opening is not mixed with moist air before it is introduced into the external auditory canal. The proximal end of the guide pane or the proximal end of the guide pane bottom and/or the guide pane frames, in this case, contact an inner side of the ear funnel in order to separate the inflow opening and the outflow opening in a fluid manner from one another.

According to an additional preferred embodiment of the present teaching, it is foreseen that the tongue-type guide pane divides an inner volume of the ear funnel into a ventilating duct for air flowing out of the attachment into the auditory canal as well as an exhaust air duct for air flowing out of the auditory canal into the attachment, wherein preferably the ventilating duct connects the connection piece with the outflow opening and wherein preferably the exhaust air duct connects the inflow opening with an outlet of the attachment.

As a result, the dry air flow and the moist air issuing out of the external auditory canal are conducted as far as possible separately from one another in the attachment. The dry air flow, preferably a warm air flow, is thus first generated by the device for generating an air flow, conducted by the connection piece and the guide pane through the ventilation duct of the ear funnel and guided into the external auditory canal. After the drying of the external auditory canal, in particular in the Recessus meatus acustici externi, the moist air can leave the external auditory canal by the inflow opening and is guided by the exhaust air duct to the outlet of the ear funnel, through which outlet the moist air is ejected from the attachment. Inside the attachment, there is thus no mixing, or only some very limited mixing, of the air masses conducted in the ventilation duct and in the exhaust air duct, causing a further increase in the efficiency of the drying.

In general, the guide pane bottom or the guide pane frames can contact the ear funnel, in particular the interior of the ear funnel, either at no point or over the entire length of the ear funnel or only in the area of the proximal opening of the ear funnel. Variants in embodiments are also conceivable in which the guide pane bottom or the guide pane frames contact the ear funnel partially and in some portions are at a distance from the ear funnel, in particular from its interior.

According to an additional preferred embodiment, it is foreseen that a cross-section of the ventilation duct decreases as it proceeds in the flow direction.

The streaming direction here is that direction in which the air flow flows through the ventilation duct in order to reach the external auditory canal. Because of this cross-section narrowing of the ventilation duct, which preferably is of continuous configuration, the outlet speed at which the air flow leaves the attachment can be adjusted and an outlet speed that is particularly advantageous for the desired drying effect can be selected.

The dimensions of the attachment have the effect that the outlet of the attachment becomes situated outside the external auditory canal. Here the outlet, especially preferably, is formed by an opening in a housing wall of the ear funnel, preferably in a portion of the ear funnel that is situated directly ahead of the connection piece.

The moist air that has already been used for drying, or the fluid that has flowed through the auditory canal, is therefore no longer directed into the connection piece or even into the device, but instead leaves the attachment earlier, in the area of the ear funnel. The result is an additional simplification of the structure of the attachment and also of the device itself. In particular, thanks to this measure, manufacturing costs of the attachment can be kept low. Because of the arrangement of the outlet in the portion of the ear funnel situated ahead of the connection piece, the outlet, in addition, can be produced in an especially simple manner. Thus, the outlet is arranged in a portion of the ear funnel, which portion, in the intended use of the attachment, extends onto the subject's external auditory canal, at least partially, preferably completely.

According to the present teaching, the attachment, moreover, can be configured in such a way that the connection piece and the guide pane are configured together as a single unit, and preferably can be combined as a unit with the ear funnel, or that the ear funnel and the guide pane are configured together as a single unit, and preferably can be combined as a unit with the connection piece, or that the connection piece, the guide vane and the ear funnel can be configured together as a single unit.

In the event of the one-piece configuration of connection piece and guide pane, variously configured ear funnels can be used in connection with the same unit including the connection piece and the guide pane, which unit can then be produced as a separate replacement part. Thus, the attachment can be adapted to various auditory canals, without a corresponding need to replace the connection piece or the guide pane. This is particularly advantageous because the configuration of the connection piece, above all according to the size and shape of an outlet opening for the air or fluid stream, is based on the device and thus is adjusted to the device used at any time. Consequently, the ear funnel, independently of the other components of the attachment, can be adapted specially to the respective user group. For example, the material, size and/or shape of the ear funnel can be selected depending on whether the attachment is to be used by female or male adults or children, while the other components of the attachment are adapted to the respective device, in connection with which the attachment is to be used. Thus, is the ear funnel easily exchangeable and, independently of other components of the attachment, can be resupplied. The possibility of replacing the ear funnel after each completed treatment of the ear, in addition, is also very favorable from the hygienic standpoint.

In the event of the one-piece configuration of the ear funnel and guide pane, all parts of the attachment that, in the intended use of the attachment, (can) come into contact with the subject's external auditory canal, namely the ear funnel and guide pane, can be supplied as a separate replacement part and can be connected with the connection piece. This makes possible an especially hygienic use of the inventive attachment, because the unit including the ear funnel and guide pane can be exchanged after every use.

In the event of the one-piece configuration of ear funnel, guide pane and connection piece, the entire attachment can be supplied as a separate replacement part and can be replaced after every use. This embodiment, in addition, is very cost-efficient.

According to an additional embodiment, it is foreseen that the connection piece is configured by an end portion of the ear funnel.

In particular, in the event of a one-piece configuration of the ear funnel, guide pane and connection piece, thanks to the resulting omission of an additional separate component, the inventive attachment can be configured more compactly and produced more cost-effectively.

The object on which the present teaching is based is also achieved by means of an ear-drying instrument including a device for generating an air flow, preferably a warm air flow, as well as an inventive attachment according to the embodiments previously described.

Analogously, an additional object of the present teaching is fulfilled by a device for care or therapeutic treatment of the external auditory canal of a human or animal ear, including an apparatus for emitting a fluid as well as an inventive attachment according to one of the embodiments previously described.

In a preferred embodiment of the inventive attachment, it is foreseen that the connection piece is designed to connect the attachment twistably to the device.

The orientation of the attachment, and thereby also the direction from which the (warm) air or fluid streams into the auditory canal, can thus, depending on the concrete application case (drying, cerumen removal, dispensing of a fluid for care or therapeutic treatment into the auditory canal) be selected or adjusted to the personal needs of the subject.

It is particularly advantageous here if the connection piece comprises on an external sleeve surface at least one indentation, which indentation can be brought into engagement with at least one clasping hook of the apparatus, in order to block the attachment in a particular twisting position on the device.

Thereby a particular twisting position of the attachment, which is optimal for instance for drying the auditory canal, can be pre-set; the attachment can additionally be easily moved into other twisting positions, but is clasped in the pre-set twisting position with the clasping hook of the device. The clasping hook, for instance, can be positioned on an inner side of the device in the area of the outlet opening of the device for the fluid stream.

Particularly preferably, several indentations at a distance from one another are made in the external sleeve surface of the connection piece in order to allow blocking of the attachment in various twisting positions on the device.

Thus, various twisting positions can be pre-set, of which for example one is optimal for a particular type of application (drying, cerumen removal, dispensing of a care or therapeutic fluid into the auditory canal).

The individual indentations preferably are placed at an angle of 180°, preferably of 90°, particularly preferably of 45° from one another. This means that at each angle position of 180°, two equidistant indentations can be positioned on the external sleeve surface of the connection piece, while for 90° the number of indentations is four and for 45° it is eight Accordingly, the attachment can be blocked in different, selected twisting positions on the device.

To allow the (warm) air or fluid stream to be introduced even more advantageously into the subject's external auditory canal, it is foreseen in another preferred embodiment of the inventive attachment that at least one inflow element is foreseen, which inflow element extended out of the guide vane bottom in order to swirl the fluid flowing out of the device and through the attachment.

Such an inflow element thus serves as a flow swirler, by which the essentially contiguous flow of the fluid through the attachment is swirled; after the inflow element passes, the stream executes a rotating motion (vortex). Such a streaming, modified by one or more inflow elements, has the effect that the advantageous drying, cleaning and therapeutic effects described above are further reinforced.

Preferably, at least two inflow elements, especially preferably flat-configured elements, are foreseen, which are arranged opposite one another on the guide vane bottom.

Thus, the inflow elements can be aligned approximately in the fluid's streaming direction or in the lengthwise direction of the attachment.

The fluid stream flowing into the attachment through the connection piece is swirled by the inflow elements, wherein, as a result of the arrangement in opposite pairs in the area of the attachment situated between the inflow elements, there is a concentration of the fluid stream, which is advantageous for the desired effects in connection with the drying, cerumen removal or dispensing of care or therapeutic fluid into the auditory canal.

In another preferred embodiment, the inflow elements have the shape of a triangle, which is preferably right-angled.

Here the inflow elements can be fastened with one side of the triangle to the guide vane bottom in such a way that the other leg faces the proximal end of the guide vane bottom and the fluid stream flowing into the attachment through the connection piece is forced by the hypotenuse of the triangle into a turbulent stream or turbulence.

Particularly preferably, inflow surfaces of the inflow elements, which inflow surfaces face the connection piece, are perpendicular to one another.

Thus, the inflow surfaces face the fluid stream entering the attachment from the device. A collision of the fluid stream on the inflow surfaces results in an especially advantageous diversion of the fluid stream (previously approximately contiguous with the guide pane bottom) in the attachment.

In another preferred embodiment of the inventive attachment, it is foreseen that, as viewed from the connection piece, a distance between opposite inflow elements decreases in the lengthwise direction of the attachment.

The fluid stream caused by inflow elements of this configuration has approximately two turbulent streams, wherein each of these eddies is caused by one of the inflow elements. Owing to the proximity of the opposite-facing pairs of inflow elements in the lengthwise direction of the attachment—and thus in the flow direction of the fluid—there is a streaming distribution in the auditory canal that is particularly favorable for the desired applications.

In another preferred embodiment of the inventive attachment, the guide vane bottom, at least in the area of a second lengthwise section of the guide vane bottom, preferably its second portion, rotates with respect to a first lengthwise section, preferably the first portion.

For example, the guide vane bottom can be configured similarly to a geometric rule as (hyper) flat, so that the second lengthwise portion, preferably an apex of the second lengthwise portion, is pushed with respect to the first lengthwise portion, preferably an apex of the first lengthwise portion, along a curve running perpendicular to the lengthwise axis of the attachment and/or the orientation of the second lengthwise portion departs from that of the first lengthwise portion.

It thereby becomes possible in a targeted manner to cause an eddy in the fluid stream introduced in the auditory canal. The resulting distribution of the streaming of the fluid flow causes an especially effective drying or cleaning of the auditory canal. Care or therapeutic liquid introduced via the attachment into the auditory canal, can also be better distributed in the auditory canal and thus can also reach sites that cannot be treated with known treatment methods.

It can be advantageous here if the first guide vane frame and the second guide vane frame, in particular opposite-situated portions of the guide vane frames, each are of different height.

Although the advantageous effects associated with embodiments described heretofore as preferred act together with the inventively configured guide pane, the corresponding advantages can also be achieved independently of the special form of the guide pane or of the guide pane bottom. In particular, the following embodiments are also part of the inventive concept:

Attachment for a device for generating an air flow, preferably a warm air flow, or for emitting a fluid, which attachment is designed to be introduced, at least partially, into an external auditory canal of a human or animal ear, wherein the attachment comprises a connection piece for connecting to the device, as well as a tongue-type guide pane having a guide pane bottom for guiding a fluid stream flowing from the device, and wherein the connection piece is designed to connect the attachment twistably on the device, wherein preferably the connection piece comprises on the enclosure service at least one indentation, which indentation can be brought into engagement with at least one connecting hook of the device, in order to block the attachment in a particular twisting position on the device, wherein preferably several indentations are set apart from one another on the external enclosure surface of the connection piece in order to be able to block the attachment in various twisting positions on the device, wherein preferably the indentations at a distance from one another of 180°, preferably 90°, especially preferably 45°.

Attachment for a device for generating an air flow, preferably a warm air flow, or for emitting a fluid, which attachment is designed to be introduced, at least partially, into an external auditory canal of a human or animal ear, wherein the attachment comprises a connection piece for connecting to the device, as well as a tongue-type guide pane having a guide pane bottom for guiding a fluid stream flowing from the device, and wherein the connection piece is designed to connect the attachment twistably on the device, wherein preferably the connection piece comprises on the enclosure surface at least one indentation, which indentation can be brought into engagement with at least one connecting hook of the device, in order to block the attachment in a particular twisting position on the device, wherein preferably several indentations are set apart from one another on the external enclosure surface of the connection piece in order to be able to block the attachment in various twisting positions on the device, wherein preferably the indentations are at a distance from one another of 180°, preferably 90°, especially preferably 45°.

Attachment for a device for generating an air flow, preferably a warm air flow, or for emitting a fluid, which attachment is designed to be introduced, at least partially, into an external auditory canal of a human or animal ear, wherein the attachment comprises a connection piece for connecting to the device, as well as a tongue-type guide pane having a guide pane bottom for guiding a fluid stream flowing from the device, and wherein at least one inflow element is foreseen, which inflow element extends out of the guide pane bottom in order to agitate the fluid streaming out of the device, wherein preferably at least two inflow elements, preferably of flat configuration, are foreseen, which are arranged opposite one another on the guide pane bottom, wherein preferably the inflow elements have the shape of a triangle, preferably a right-angle triangle, wherein preferably inflow surfaces of the inflow elements, which inflow surfaces face the connection piece, run perpendicularly to one another, wherein preferably a distance between the opposite-situated inflow elements, viewed from the connection piece, decrease in the lengthwise direction of the attachment.

Attachment for a device for generating an air flow, preferably a warm air flow, or for emitting a fluid, which attachment is designed to be introduced, at least partially, into an external auditory canal of a human or animal ear, wherein the attachment comprises a connection piece for connecting to the device, as well as a tongue-type guide pane having a guide pane bottom for guiding a fluid stream flowing from the device, and wherein the guide pane bottom is twisted with respect to the first lengthwise portion, at least in the area of a second lengthwise portion, whereby preferably the first guide pane frame and the second guide pane frame have a different height in each case.

BRIEF DESCRIPTION OF THE DRAWINGS

The present teaching is now more closely described with reference to embodiments. The drawings are exemplary and intended to expound the inventive concept, without restricting it in any way or finally reproducing it. The figures are as follows:

FIG. 7a shows a line depiction of FIG. 1a.
FIG. 7c shows a line depiction of FIG. 2a.

FIG. 9b shows detail G from FIG. 9a.

FIG. 13a shows a perspective view of the attachment from FIG. 12a.

FIG. 13b shows a second perspective view of the attachment from FIG. 12a.

FIG. 13c shows a third perspective view of the attachment from FIG. 12a.

DETAILED DESCRIPTION

Figure 1A:
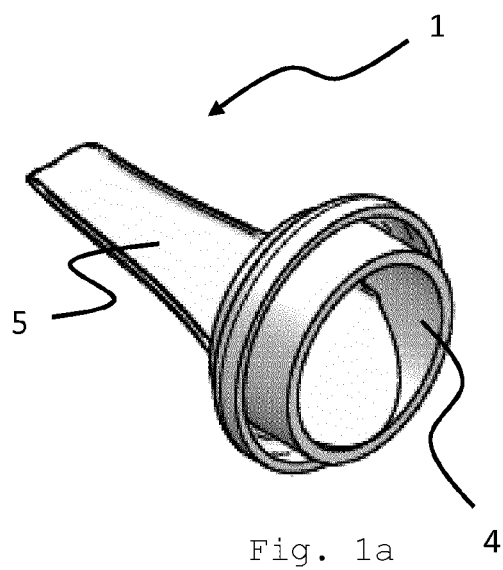
FIG. 1a shows an inventive attachment in a first embodiment.

In the following description, the term "lengthwise section" designates a section through an inventive attachment 1, in which the sectional plane runs parallel to the sectional plane of the figures and a lengthwise axis 12 of the attachment 1 is situated in the sectional plane. In addition, the term "cross-section" designates a section through the attachment 1 in which the sectional plane runs orthogonally to the lengthwise section.

In principle, a number of conceivable embodiments of the inventive attachment exist, wherein it is common to all these embodiments that an air flow is agitated and/or is reflected because of the guide pane structure on lateral walls of a subject's exterior auditory canal 3, in order to cause an optimal drying effect inside the eternal auditory canal 3.

In a first embodiment, the inventive attachment 1 includes a connection piece 4 as well as a tongue-type guide pane 5, and in addition can optimally include an ear funnel 18, wherein the connection piece 4 and the guide pane 5 are configured as forming a single unit and can be dissolubly connected with the ear funnel 18. This embodiment is distinguished, among other ways, in that the ear funnel 18 is removable and the attachment 1 can be used with or without ear funnel 18. The ear funnel 18, which is not necessarily foreseen in this embodiment—when present—is easily exchangeable and, depending on the connection piece 4 and the guide pane 5, can be replaced. The possibility of exchanging the ear funnel 18 after every drying process is, in addition, also very reasonable in a hygienic sense.

In a second embodiment, the inventive attachment likewise includes the connection piece, the guide pane and the ear funnel, wherein the ear funnel and the guide pane in this embodiment are of configured as forming a single unit and the combination of ear funnel and guide pane can be combined with the connection piece. Here, all parts of the attachment that, in the intended use of the attachment, (can) come into contact with the subject's external auditory canal 3, namely ear funnel and guide pane, can be supplied as separate replaceable part and combined with the connection piece. This allows an especially hygienic use of the inventive attachment, because the unit including the ear funnel and the guide pane can be exchanged after each use.

In a third embodiment, the inventive attachment likewise includes the connection piece, the guide pane and the ear funnel, wherein the connection piece, guide pane and ear funnel in this embodiment are configured together as a single unit. The entire attachment can thereby be supplied as a separate replacement part and can be exchanged after each use. The result is especially simple and hygienic handling of the attachment according to the third embodiment. In addition, the attachment can be especially simple and thereby inexpensive to produce owing to its one-piece configuration.

Likewise included in the inventive concept are embodiments of the attachment in which the connection piece, the guide pane and the ear funnel are each configured as a separate component.

In the following discussion, the present teaching is described in greater detail with reference to the first embodiment of the inventive attachment 1 illustrated in FIGS. 1 through 6; the second and third embodiments, on the other hand, are not illustrated in FIGS. 1 through 6.

FIG. 1a is a perspective depiction of this embodiment of the inventive attachment 1 without ear funnel, which is optional in this embodiment. The attachment 1 includes the connection piece 4 for connecting the attachment 1 to a device 2 for generating air flow, preferably a warm air flow, or for dispensing a fluid. The connection piece 4 here constitutes a portion of the attachment 1, which ensures that the attachment 1 adheres to the device 2.

In addition, the attachment 1 includes the tongue-type guide pane 5, which can be introduced into an external auditory canal 3 of an animal or human (hereinafter referred to as the subject) for the purpose of drying the auditory canal 3 (see FIG. 6). The guide pane 5 makes possible the controlled guidance of the air flow as well as its controlled dispensing to the external auditory canal 3. The guide pane 5 comprises a guide pane bottom 25 for guiding the air flow and in addition can include guide pane frames 26 in order to configure a guide duct or a part of a guide duct for the air flow.

Figure 3A:
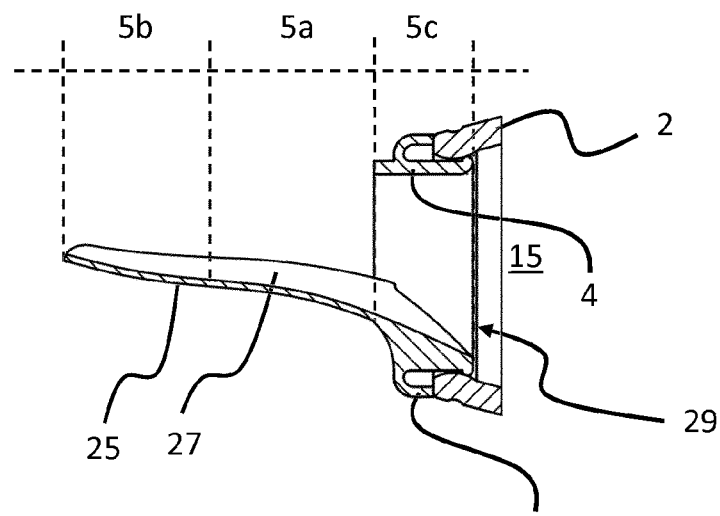
FIG. 3a shows a lengthwise section through the attachment from FIGS. 2a and 2b, which is fastened on a device for generating an air flow or for emitting a fluid.
Figure 3B:
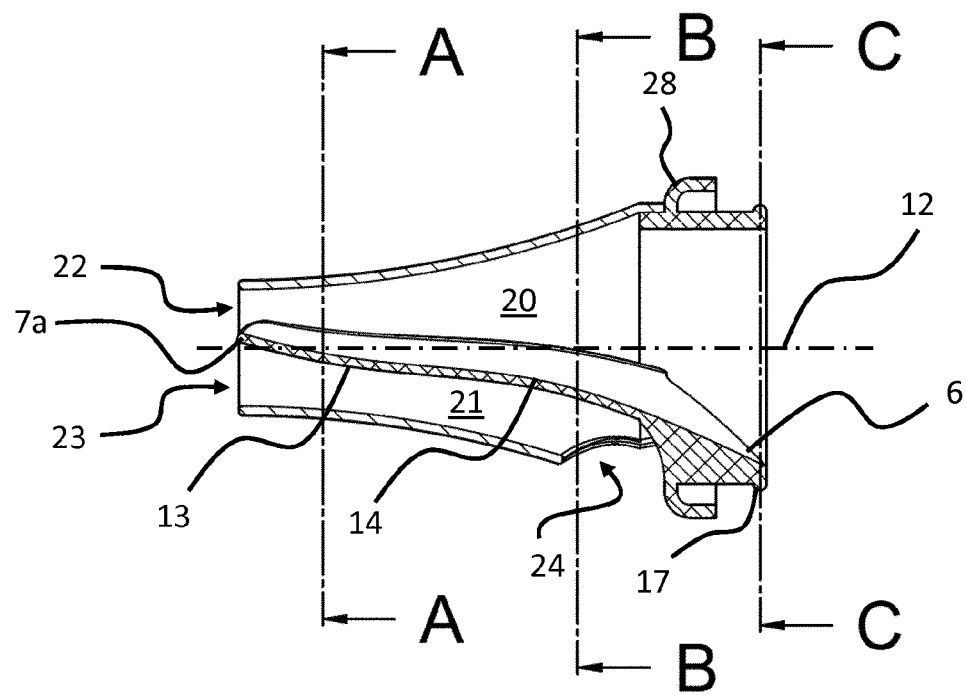
FIG. 3b shows a lengthwise section through the attachment from FIGS. 2a and 2b.

FIG. 3a shows a lengthwise section of the inventive attachment 1 according to a first embodiment without ear funnel, which lengthwise section runs through the connection piece 4 and the guide pane 5. FIG. 3b shows the attachment 1 from FIG. 3a with ear funnel 18, wherein the attachments 1 shown in FIGS. 3a and 3b are of identical configuration even including the ear funnel 18.

The essentially sleeve-shaped connection piece 4 serves to connect the attachment 1 to the device 2 and makes possible the inflow of the air flow from the device 2 into the attachment 1.

The structure of the connection piece 4 is based here on the structure of an outlet opening 15 of the device 2, through which outlet opening 15 the air flow from the device 2 flows out. The tongue-type guide pane 5 is set apart from the connection piece 4 and guides the air flow into the subject's external auditory canal 3 (see FIG. 6).

To be able to use the attachment 1, illustrated in FIG. 3a, as intended, for drying the external auditory canal 3, the latter can be introduced with the guide pane 5—either partially or completely—into the subject's external auditory canal 3.

From FIGS. 3a and 3b it is clearly visible that the guide pane 5 is arranged so that the guide pane bottom 25 intersects the lengthwise axis 12 of the attachment 1. The lengthwise axis 12 of the attachment 1 runs through a center point of a cross-section of the connection piece 4 shown standing perpendicularly on the lengthwise section show in FIGS. 3a and 3b. The cross-section of the connection piece 4 refers here exclusively to the connection piece 4 itself—thus, in particular, not to any portions of the guide pane 5 arranged inside the connection piece 4. The cross-section of the connection piece 4, through whose center point the lengthwise axis 12 extends, is shown in FIG. 4c.

As a result of this arrangement of the guide pane 5, the air flow is conducted into the subject's external auditory canal 3 in such a way that an especially advantageous streaming field for the desired drying effect develops in the external auditory canal 3. In addition, it can thereby be ensured that the air flow issuing from the attachment 1 is not conducted directly to the subject's eardrum 31. To be precise, the air flow, if it flows via a proximal end 7a of the guide pane bottom 25 and leaves the attachment 1, is agitated and/or introduced into the external auditory canal 3 in such a way that the air flow is reflected onto the lateral walls of the external auditory canal 3 in order to cause an optimal drying effect in the interior of the external auditory canal 3. The guide pane bottom 25 preferably intersects the lengthwise axis 12 in a proximal—because it is closest to the subject's eardrum 31—end portion of the attachment 1.

Figure 4A:
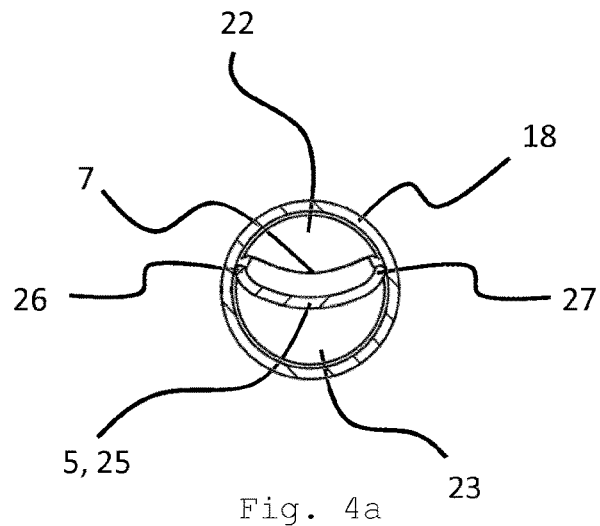
FIG. 4a shows a cross-section of the attachment from FIG. 3b according to A-A.
Figure 4B:
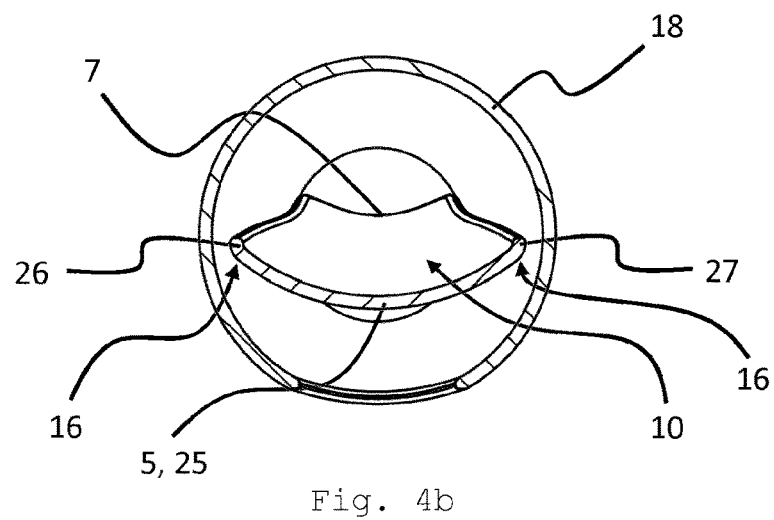
FIG. 4b shows a cross-section of the attachment from FIG. 3b according to B-B.
Figure 4C:
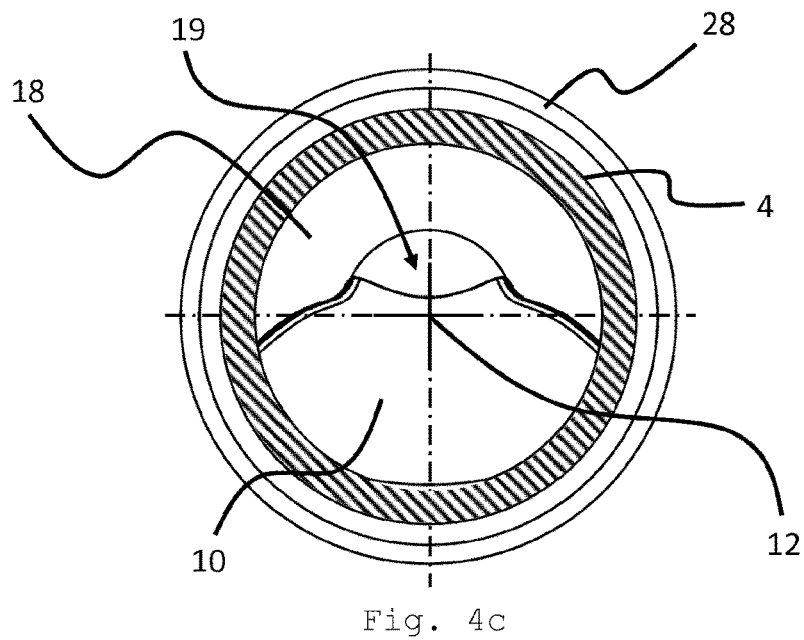
FIG. 4c shows a cross-section of the attachment from FIG. 3b according to C-C.

It can likewise be seen from FIGS. 3a and 3b that the guide pane bottom 25 comprises a curved lengthwise section, which stands perpendicularly to the cross-section of the guide pane bottom 25 illustrated in FIGS. 4a and 4b. The guide pane bottom 25 of a first portion 5a of the guide pane 5 standing apart from the connection piece 4 comprises a lengthwise cross-section course, which is curved in a first direction, and the guide pane bottom 25 of a second portion 5b of the guide pane 5 standing apart from the connection piece 4 has a lengthwise section course, which is curved in a second direction, wherein the two curved portions 5a, 5b run in a curve opposite one another. In the embodiment shown in FIGS. 3a and 3b, the second portion 5b has a proximal end 7 of the guide pane 5.

Thus, the guide pane 5 comprises at least a first apex 13 and a second apex 14. As a result of this special course of the guide pane 5, an especially favorable stream distribution of the air flow is achieved inside the external auditory canal 3. In this embodiment of the present teaching, especially good results were obtained in the drying, especially in comparison with attachments that included a guide pane 5 with a straight lengthwise cross-section course. It is especially advantageous if—as viewed from the connection piece 4—the gradient of a tangent applied on the guide pane bottom 25 in the first portion 5a of the guide pane bottom 25 decreases with the distance from the connection piece 4 and increases in the second portion 5b of the guide pane bottom 25 with the distance from the connection piece 4.

The guide pane 5 comprises a portion 5c running in the connection piece 4, wherein the portion 5c comprises a distal—because at a distance from the subject's eardrum 31—end 6 of the guide pane 5. The portion 5c continues the portion 5a of the guide pane 5. A streaming cross-section for air flowing out of the device 2 into the attachment. 1 is bounded by the portion 5c of the guide pane 5 running in the connection piece 4 and the connection piece 4. Every part of the entire air stream that is intended to proceed unhindered from the connection piece 4 to the guide pane 5 can thereby be adjustable. In particular, the air stream can thereby be subjected to a streaming cross-section narrowing, which streaming cross-section narrowing can be omitted less drastically from attachments for children, for example, than from attachments for adults. The portion 5c of the guide pane 5 running in the connection piece 4, in addition, makes it possible to absorb the air flow streaming in from the device 2 into the attachment 1 already in the area of the connection piece 4, so that the air flow can be guided accordingly immediately upon entry into the attachment 1.

Two guide pane frames stand apart from the lengthwise side edges 16 of the guide pane bottom 25, namely a first guide pane frame 26 and a second guide pane frame 27, to configure, jointly with the guide pane bottom 25, a guide duct 10 or part of a guide duct 10 for the air flow. The guide pane bottom 25 and guide pane frames 26, 27 then form part of the guide duct 10 if the guide pane frames 26, 27 stand apart only in a lengthwise portion of the guide pane 5, but not over its entire length. The guide duct 10 configured by the guide pane bottom 25 and guide pane frames 26, 27 for the air flow is configured by that volume that is bounded by the guide pane bottom 25, first guide pane frame 26 on the one hand and the second guide pane frame 7 on the other hand. Targeted and controlled guidance of the air flow inside the attachment 1 as well as controlled dispensing of the air flow to the external auditory canal 3 can be further improved by the guide duct 10. In addition—with embodiments having an ear funnel, such as in the case of the first embodiment of the attachment 1 with ear funnel 18 according to FIG. 3b—any kind of undesired reflections of the air flow on an inner wall of the ear funnel 18 can be avoided by using the guide pane frames 26, 27.

FIG. 4a shows the cross-section of the inventive attachment 1 according to section line A-A from FIG. 3b. FIG. 4b shows the cross-section according to section line B-B from FIG. 3b. The section runs in both cases through the ear funnel 18 as well as through the guide pane bottom 25 of the guide pane 5. FIG. 4c shows the cross-section of the connection piece 4 according to section line C-C from FIG. 3b.

As can be seen in FIGS. 4a, 4b, the guide pane bottom 25 comprises a preferably U-shaped, curved cross-section profile in the illustrated embodiment. Here the cross-section of the guide pane bottom 25 over the entire length of the guide pane 5 is curved in a slightly U-shape. The curvature here can increase or decrease from one end of the guide pane 5 to the other end of the guide pane 5. It can also be foreseen that the cross-section of the guide pane bottom 25 is curved not over the entire length of the guide pane 5 but rather only in a lengthwise portion of the guide pane 5. Curves of the cross-section profile of the guide pane bottom 25 are also conceivable in other than U-shape. FIGS. 4a and 4b show cross-sections of the attachment 1 with ear funnel 18 according to FIG. 3b; however, because the attachment 1 shown in FIG. 3b is identical to the attachment 1 shown in FIG. 3a, aside from the ear funnel 18, the comments made concerning the curved cross-section profile of the guide pane bottom 25 also apply to the first embodiment of the attachment 1 without ear funnel 18, as in FIG. 3a.

The attachment 1 according to the first embodiment can be introduced into the external auditory canal 3 either without or with the ear funnel 18 in order to be employed as intended for drying the external auditory canal 3.

Figure 1B:
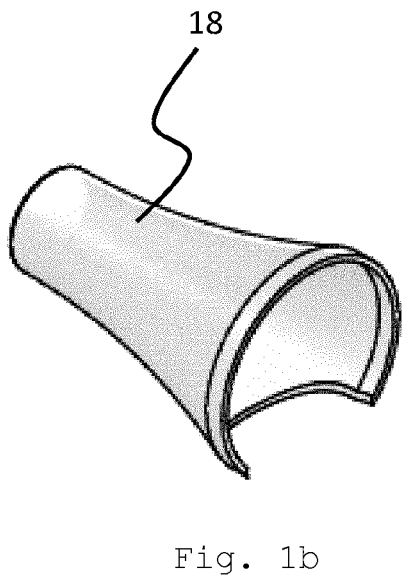
FIG. 1b shows an ear funnel of the first embodiment of the inventive attachment.
Figure 2A:
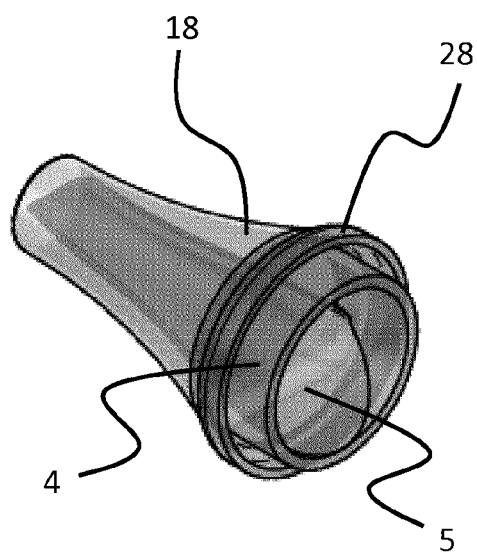
FIG. 2a shows the first embodiment of the attachment with ear funnel in a first perspective view.
Figure 2B:
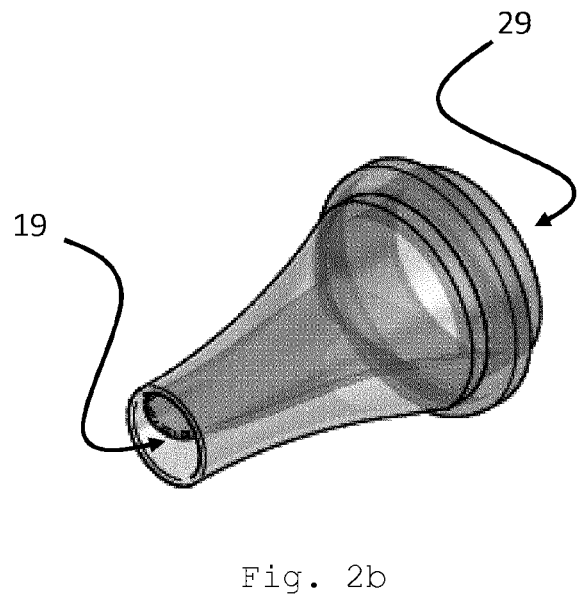
FIG. 2b shows the first embodiment of the attachment with ear funnel in a second perspective view.

Because of the dissoluble connecting of the attachment 1 shown in FIGS. 1a and 3a with the ear funnel 18 depicted in perspective in FIG. 1b, one receives in the attachment 1 shown in FIGS. 2a, 2b and 3b, namely the attachment 1 according to the first embodiment with ear funnel 18. For this purpose, the ear funnel 18 can be pushed onto the connection piece 4—or connected with this or with the guide pane in some other way. With other embodiments of the attachment 1, such as with the third embodiment, described above, the connection piece 4 can be configured by an end portion of the ear funnel 18, preferably a distal end portion.

In the case of the first embodiment of the attachment 1 with ear funnel 18, the ear funnel 18 can be connected dissolubly with the connection piece 4 and projects from it in such a way that the guide pane 5 over its entire length is enclosed by the ear funnel 18 and the connecting connection piece 4. It can also be foreseen that the ear funnel 18 connection piece 4 enclose only a lengthwise portion of the guide pane 5, so that the guide pane 5 extends outward beyond the ear funnel 18. The ear funnel 18 shown in FIG. 1b in the present embodiment is rotation symmetrical as far as an outlet 24, wherein the lengthwise axis 12 of the attachment 1 forms the corresponding rotation axis of the ear funnel 18.

From FIGS. 2a, 2b, 3b, 4a, 4b and 4c it can be clearly seen that the cross-section of the ear funnel 18 decreases in size, from the connection piece 4 to a proximal opening 19 of the ear funnel 18, by means of which the ear funnel 18 is introduced into the auditory canal 3 in an intended use of the attachment 1. This cross-section reduction makes it possible to determine the insertion depth of the attachment 1 into the external auditory canal 3. It thereby becomes possible, for instance, to move the attachment 1 to within about 15 mm, preferably approximately about 10 mm, of the subject's eardrum 31.

The proximal end 7 of the guide pane 5, or the proximal end 7a of the guide pane bottom 25, is essentially arranged flush with the proximal opening 19 of the ear funnel 18. Accordingly, the proximal end 7a of the guide pane bottom 25 is situated within the proximal end 19 of the ear funnel 18 and divides it into outflow opening 2 for air streaming out of the attachment into the external auditory canal 3, as well as an inflow opening 23, through which inflow opening 23 air can stream out of the external auditory canal 3 back into the attachment 1

With embodiments of the attachment with ear funnel, such as in the case of the first embodiment of the attachment 1 with ear funnel 18, in which the guide pane 5 projects from the connection piece 4 of the attachment 1 or is connected to it, the guide pane 5 extends essentially over the entire length of the ear funnel 18. The air stream serving for drying can thereby be directed over the entire length of the ear funnel 18 and, under close control, can be dispensed into the external auditory canal without risk of injury to the external auditory canal 3 and/or the eardrum.

To increase the efficiency of drying still further, the outflow opening 22 can be smaller than the inflow opening 23. For example, the outflow opening 22 can take up one-third of the proximal opening 19 and the inflow opening 23 can take up two-thirds of the proximal opening 19.

Because the proximal opening 19 of the ear funnel 18 is usually smaller than the distal opening 29 of the connection piece 4, drying by the air stream is further supported by an increase of the outlet speed of the air stream from the attachment 1 and the complete escape of moist air from the auditory canal 3 is ensured. By way of the distal opening of the connection piece 4, the air stream flows out of the device 2 into the attachment 1.

Among embodiments of the attachment with ear funnel, such as in the case of the first embodiment of the attachment 1 with ear funnel 18, an interior volume of the ear funnel 18 is divided by the guide pane bottom 25, and in some cases by the first guide pane frame 26 and second guide pane frame 27, into a ventilation duct 20 and an air exhaust duct 21. For this purpose, the lengthwise side borders 16 of the guide pane bottom 25, or—if present—the guide pane frames 26, 27 connected thereto, can directly contact the ear funnel 18 either along their entire length or only partially, or else can be slightly set apart from the ear funnel 18. In the case of direct contact over the entire length of the guide pane 5, fluid insulation can be established between the ventilation duct 20 and the air exhaust duct 21. In the case of only partial contact or a distance between guide pane 5 and ear funnel 18, complete insulation is guaranteed, or at least secured, so that mixing of the air directed in the ventilation duct 20 with the air directed in the exhaust air duct 21 is prevented as much as possible.

The ventilation duct 20 connects the distal opening 29 of the connection piece 4 with the outflow opening 22. The exhaust air duct 21 connects the inflow opening 23 of the ear funnel 18 with the outlet 24 of the attachment 1, which is configured on an underside of the ear funnel 18 as an indentation in its housing. Accordingly, the ventilation duct 20 makes possible the inflow of the air or fluid stream generated by the device 2 into the subject's external auditory canal 3, and the exhaust air duct 21 allows the return streaming of air used for drying the external auditory canal 3 or of the fluid used for cleansing or treatment out of the external auditory canal 3 into the atmosphere.

To prevent reshaping of the guide pane 5 during the intended use of the inventive attachment 1 if the attachment 1 is or was already introduced into the external auditory canal 3, it can be foreseen that the ear funnel 18 is rigidly configured in comparison with the connection piece 4 and/or with the guide pane 5, preferably more flexibly than the connection piece 4 and/or the tongue-type guide pane 5. By means of this action, the ear funnel 18, in particular, protects the guide pane 5 from any kind of reshaping. For example, the ear funnel 18 can be made of polyethylene or polypropylene, while the connection piece 4 and guide pane 5 can be constructed of thermoplastic elastomer or of silicone.

Figure 5A:
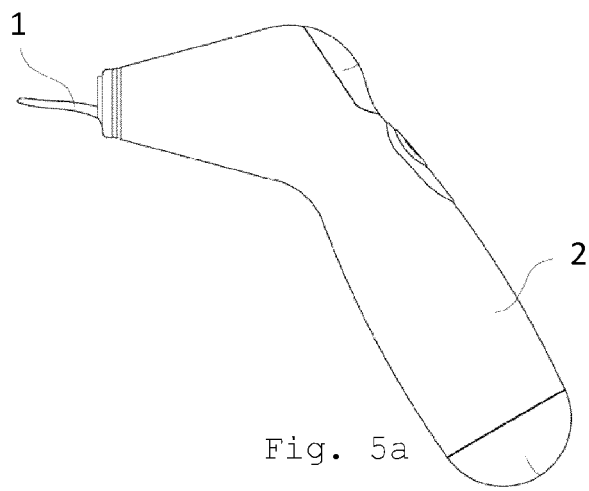
FIG. 5a shows an inventive ear-drying device including the attachment according to the first embodiment without ear funnel.
Figure 5B:
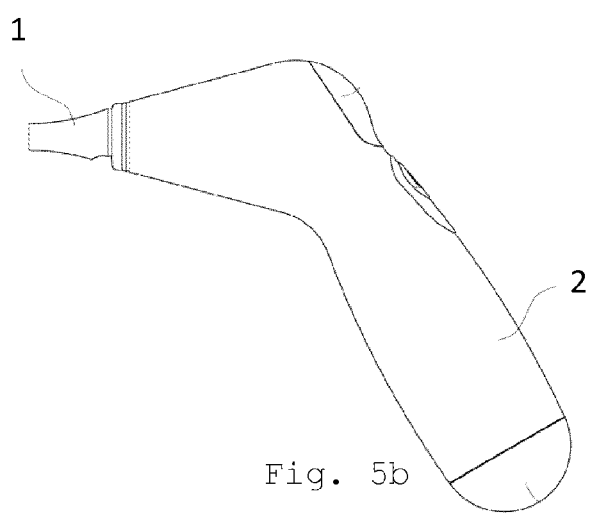
FIG. 5b shows the inventive ear-drying device including the inventive ear-drying device including the attachment according to the first embodiment with ear funnel.
Figure 5C:
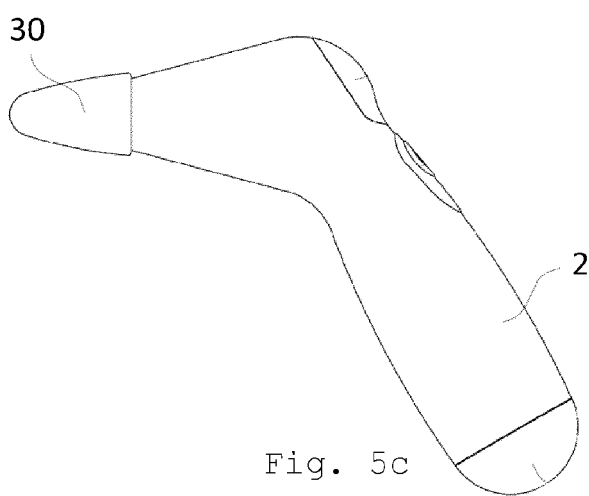
FIG. 5c shows the inventive ear-drying device with a protective cap.

FIG. 3a shows the attachment 1 in a connecting position, in which the attachment 1 is connected to the device 2 (see also FIGS. 5a, 5b and 5c).

Figure 9A:
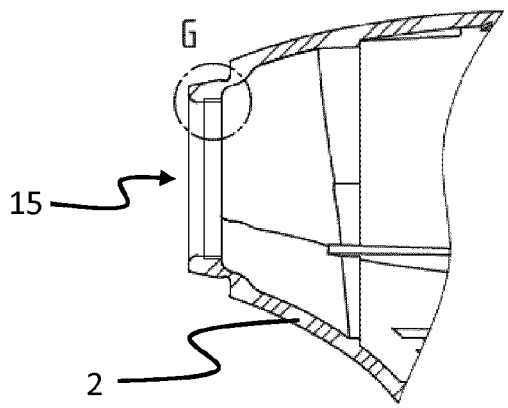
FIG. 9a shows a device for emitting a fluid in the area of an outlet opening in a section view.
Figure 9B:
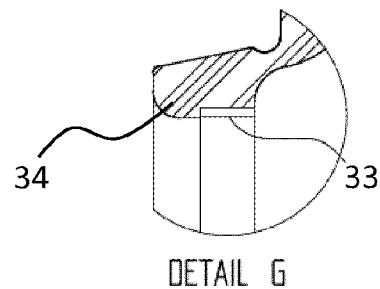

For the purpose of connection, the attachment 1 with the connection piece 4 is introduced partially into the outlet opening 15 for the air stream of the device 2. A latching protrusion 17 on an end portion of the connection piece 4 on the device is engaged with a retention portion 34 of the device 2 and thus prevents inadvertent release of the connection between the device 2 and the attachment 1 (see, for instance FIG. 6a or 9b). In principle, however, many different types of connection are conceivable for attaching the attachment 1 to the device 2. The air or water stream issuing from the device 2 thus flow first through the connection piece 4 of the attachment 1 when it flows into the attachment 1. This is also the case when the connection piece 4 is not introduced into the outlet opening 15 but rather is otherwise connected with the device 2, for example mounted onto it.

A distance holder 28, positioned to surround the circumference of the connection piece 4 at least partially, is aligned on a housing of the device 2 and thus ensures that the connection piece 4 cannot be introduced deeper than intended into the outlet opening 15. In embodiments of the attachment having an ear funnel, such as in the case of the first embodiment with ear funnel 18 according to FIG. 3b, the ear funnel 18 can be pushed onto the connection piece 4 for the purpose of connection and can be aligned with the distance holder. Here the connection piece 4 and ear funnel 18 are connected with one another by force fitting, wherein other possibilities for connection also exist—such as by means of interlocking latching recesses and latching protrusions.

FIG. 5a shows an inventive ear-drying instrument, including the device 2 for generating an air flow as well as the inventive attachment 1 according to the first embodiment of the inventive attachment, wherein the ear funnel 18 has been removed from the combined connection piece 4 and guide pane 5, which are configured as a single unit, and thus is not visible.

The device 2 is preferably designed for the purposes of drying ears and can advantageously be configured as portable.

FIG. 5b shows the inventive ear-drying instrument including the device 2 for generating an air flow as well as the inventive attachment 1 with ear funnel 18.

FIG. 5c shows the inventive ear-drying instrument from FIG. 5a or 5b. The attachment 1 here is covered by a protective cap 30, which in particular serves to protect the attachment 1 during transport of the device 2.

Figure 6A:
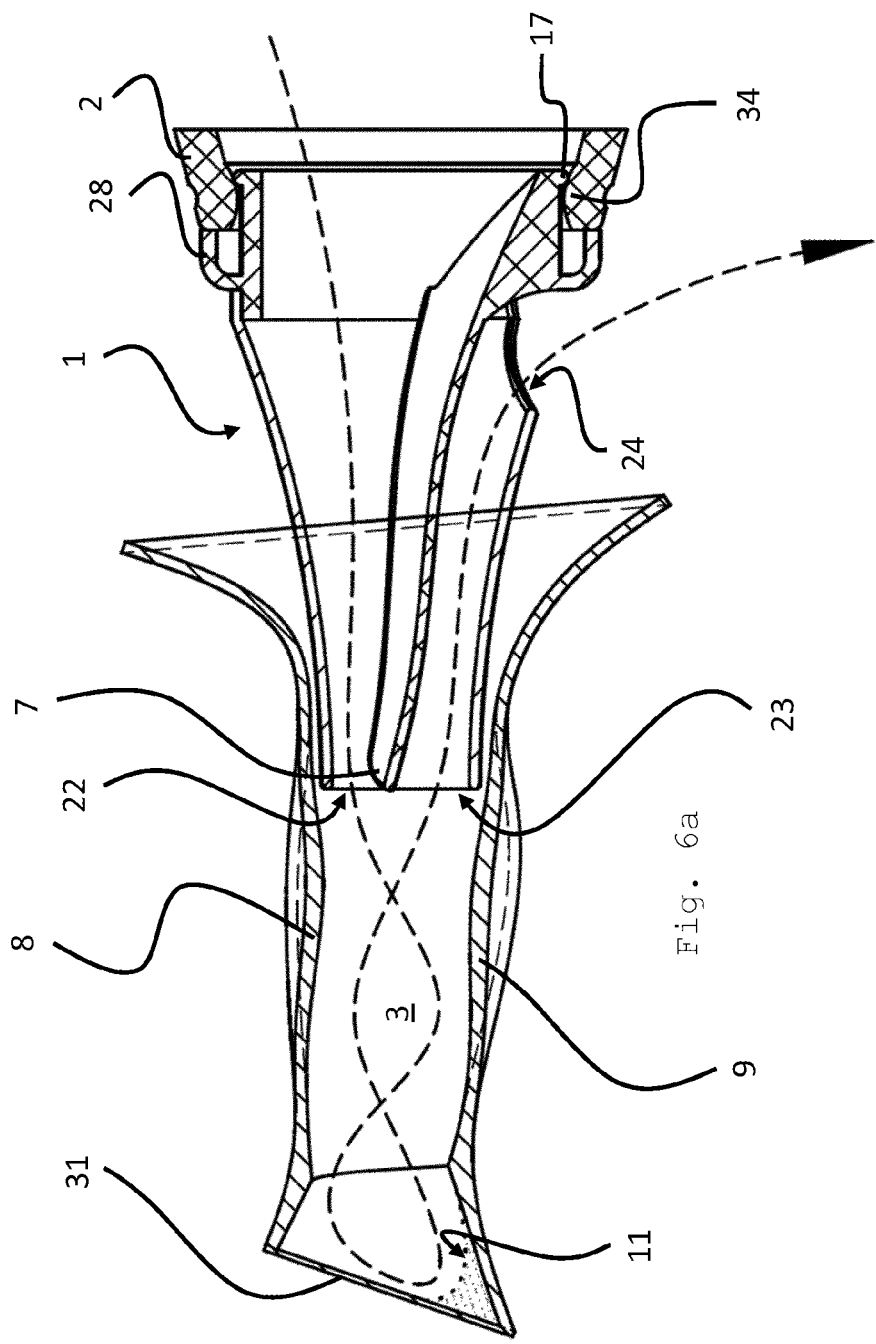
FIG. 6a shows a first streaming course in an external auditory canal determined by the inventive attachment.

FIG. 6a is a schematic depiction of the streaming pathway, determined by the attachment 1, of an inventive device in its operating position. The illustrated streaming pathway inside the external auditory canal 3 thus develops unchanged, independently of the concrete embodiment of the inventive attachment 1. Because of the comparatively large introduction depth of the attachment 1 into the external auditory canal 3, no reflection of the air flow issuing from the attachment reaches the lateral walls 8, 9; the air flow, because of the guide pane 5, is agitated on leaving the attachment 1, so that inside the external auditory canal 3, turbulence develops that is favorable for drying.

Figure 6B:
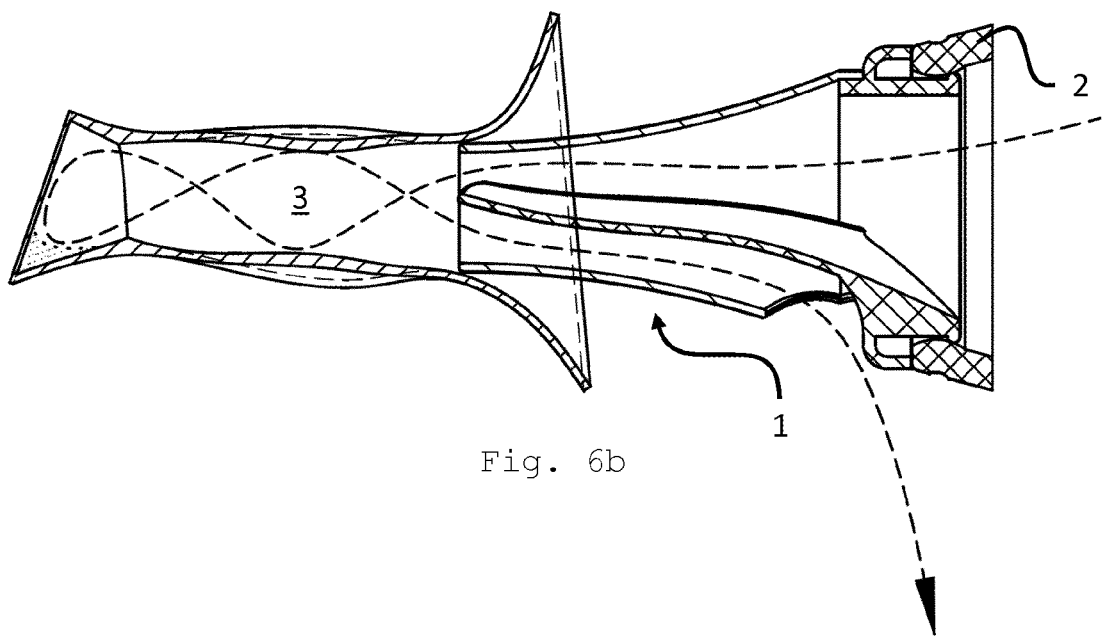
FIG. 6b shows a second streaming course in an external auditory canal determined by the inventive attachment.

FIG. 6b likewise shows the attachment 1 introduced into the auditory canal, however at a lesser insertion depth than in FIG. 6a. The result is a different flow image inside the external auditory canal 3, which again is independent of the embodiment of the attachment 1 that is selected. In this case the air flow issuing from the attachment 1 is reflected onto the lateral walls 8, 9 of the external auditory canal 3, so that inside the external auditory canal 3 turbulence develops that is favorable for drying.

Figure 6C:
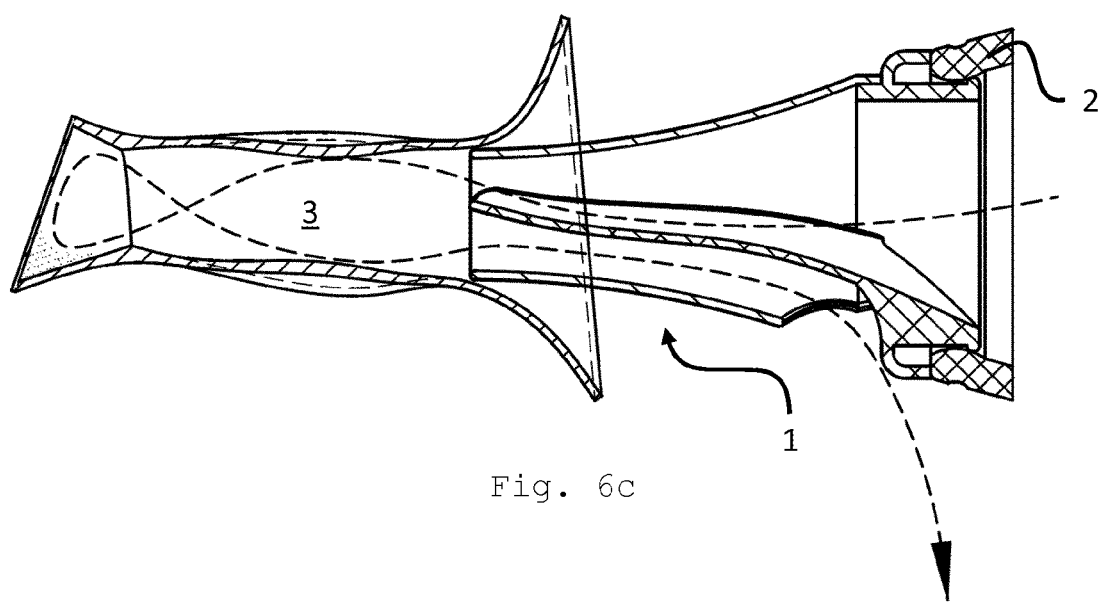
FIG. 6c shows a third streaming course in an external auditory canal determined by the inventive attachment.

FIG. 6c shows the attachment 1 inserted into the auditory canal 3, wherein the ear-drying instrument, however, is operated with other operational parameters, with the result that the outlet angle of the air flow out of the attachment 1 is different. Consequently, there is a different streaming image inside the external auditory canal 3, which, however, is again independent of the selected embodiment of the attachment 1. Also, in this case, the air stream flowing out of the attachment 1 is reflected on the lateral walls 8, 9 of the external auditory canal 3, so that an eddy favorable for drying develops inside the external auditory canal 3.

Figure 7A:
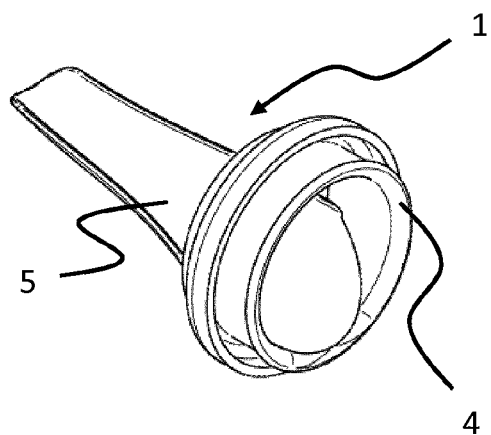
Figure 7B:
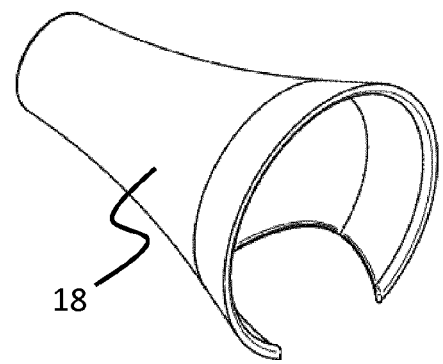
FIG. 7b shows a line depiction of FIG. 1b.
Figure 7C:
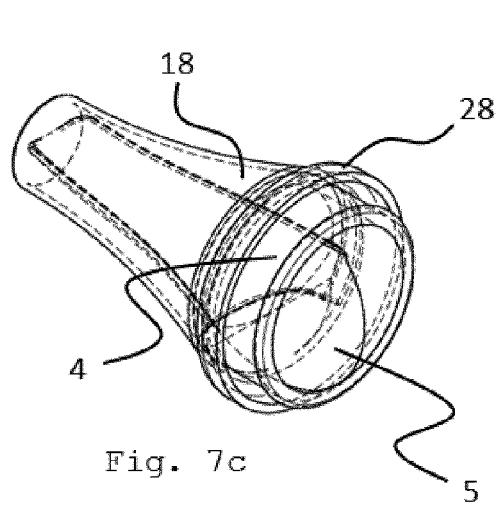
Figure 7D:
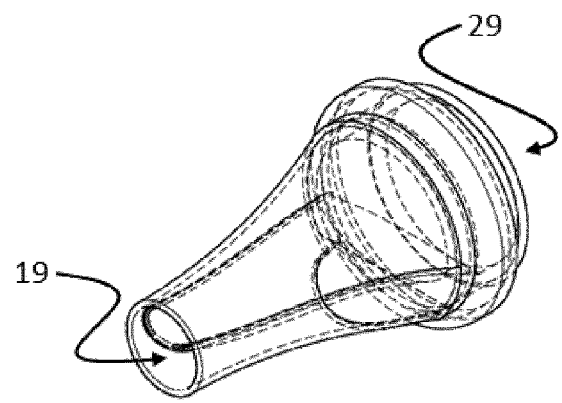
FIG. 7d shows a line depiction of FIG. 2b.
Figure 8A:
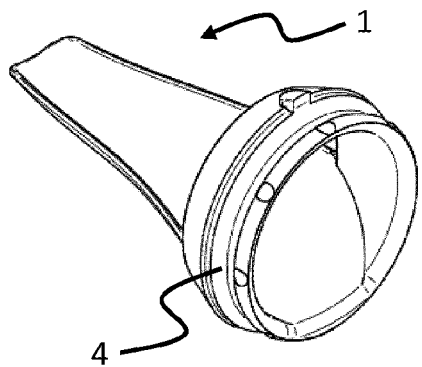
FIG. 8a shows a perspective view of an embodiment of the inventive attachment with indentations.
Figure 8B:
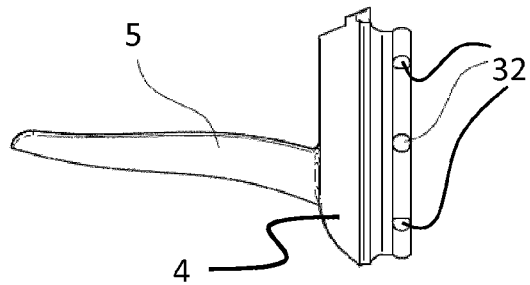
FIG. 8b shows the attachment from FIG. 8a in a lateral view.
Figure 8C:
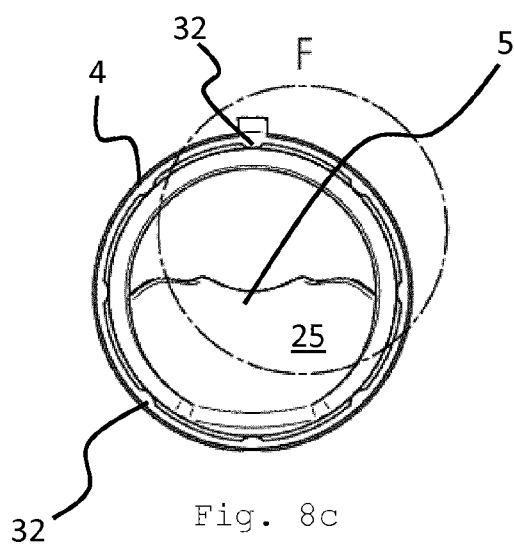
FIG. 8c shows the attachment from FIG. 8a viewed in lengthwise direction of the attachment.
Figure 8D:
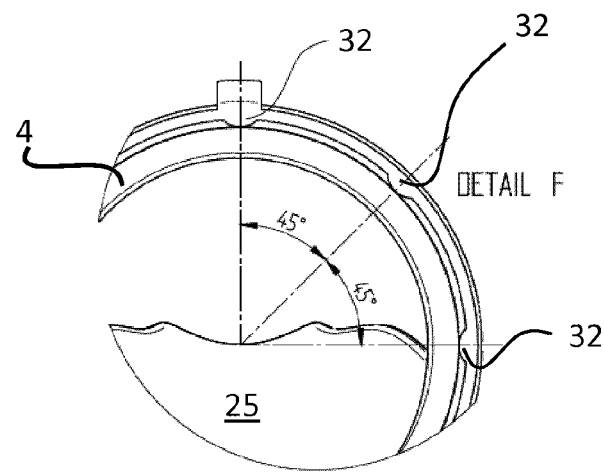
FIG. 8d shows detail F from FIG. 8c.

FIGS. 7a, 7b, 7c and 7c are each linear depictions of FIGS. 1a, 1b, 2a and 2b.

FIGS. 8a, 8b, 8c and 8d show a fourth embodiment of the inventive attachment 1. All statements made so far in connection with the first, second and third embodiments also apply to the fourth embodiment, illustrated here. In addition, the connection piece 4 of the attachment of the fourth embodiment comprises several indentations 32. The indentations in this case are arranged in the end portion of the connection piece 4 having the device, said end portion also configuring the latching protrusion 17. As can be seen from FIGS. 8c and 8d, the indentations 32 are at an angle of 45°; accordingly, a total of eight indentations 32 are arranged in the end portion of the connection piece 4.

If the attachment 1 with the end portion of the connection piece 4 is introduced into the outlet opening 15 of the device 2 in order to connect the attachment 1 with the device 2, the latching protrusion 17 of the connection piece 4, which is engaged with the retention portion 34 of the device 2, prevents unintentional release of the attachment 1 from the device 2; however, the attachment 1 can be twisted freely contrary to the device 2, so that—depending on the twisting position—various orientations of the guide pane 5 can be adopted. To block the attachment 1 in a particular twisting position on the device 2, at least one latching protrusion 33 can be foreseen on the device 2 (see FIGS. 9a and 9b), preferably in the area of the outlet opening 15, which latching protrusions 33 can be brought into engagement with one of the indentations 32. The indentations 32 thus indicate preferred twisting positions of the attachment 1 on the device 2.

Figure 10A:
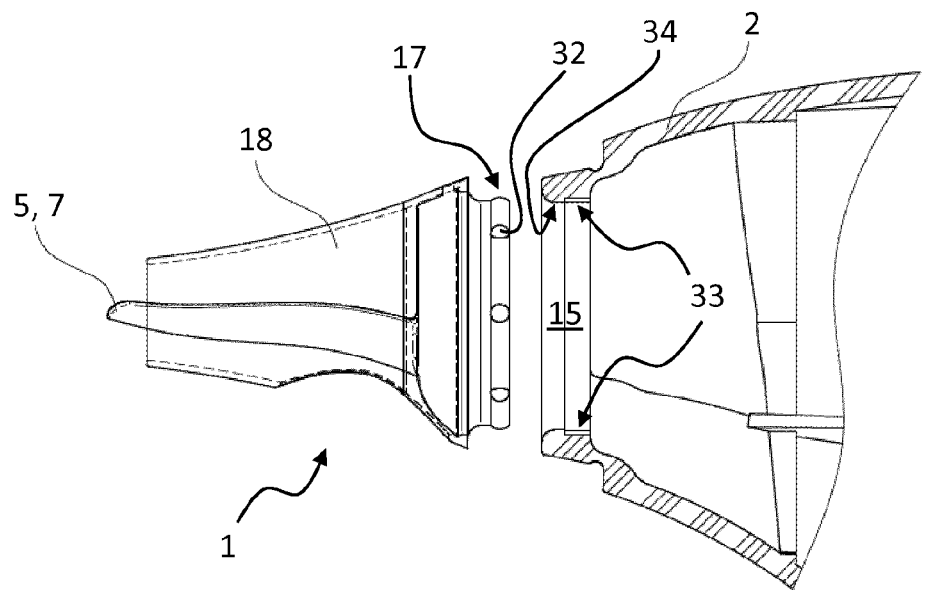
FIG. 10a shows an embodiment of the inventive attachment before the connection to a device for emitting a fluid.
Figure 10B:
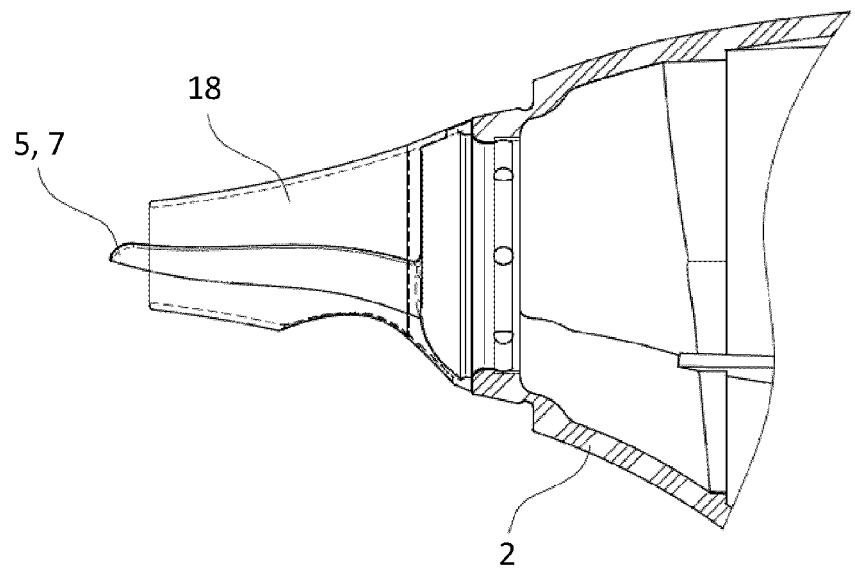
FIG. 10b shows an embodiment of the inventive attachment connected to a device for emitting a fluid.

FIG. 10*a* shows the attachment 1 before connection to the device 2 for dispensing a fluid, such as for instance air, water or another therapeutic or treating liquid. To connect the attachment 1 with the device 2, as is shown in FIG. 10*b*, the attachment 1 can be introduced into the outlet opening 15 with its device-bearing end portion. The retention portion 34 of the device 2 prevents inadvertent release of the attachment 1 from the device 2. The latching protrusion 33, at particular twisting positions of the attachment 1 corresponding to the indentations 32, can engage in the respective indentation 32 in order to secure the attachment 1 in the corresponding twisting positions. By twisting the attachment 1 out of this twisting position, the attachment 1 can be brought into a different twisting position in which the latching protrusion 33 can engage in a different latching recess 34.

Figure 11A:
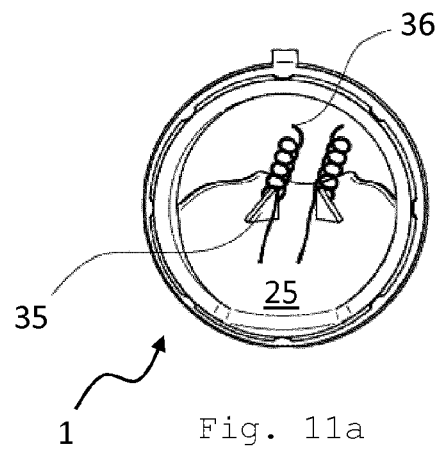
FIG. 11a shows an embodiment of the inventive attachment with inflow elements viewed in the lengthwise direction of the attachment.
Figure 11B:
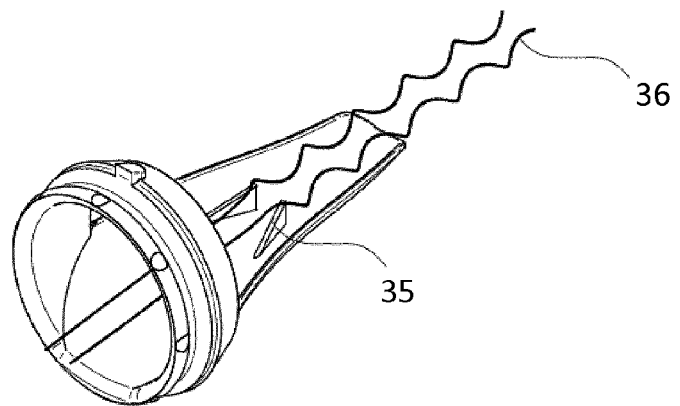
FIG. 11b shows the attachment from FIG. 11a in a perspective depiction.
Figures 12A, 12B:
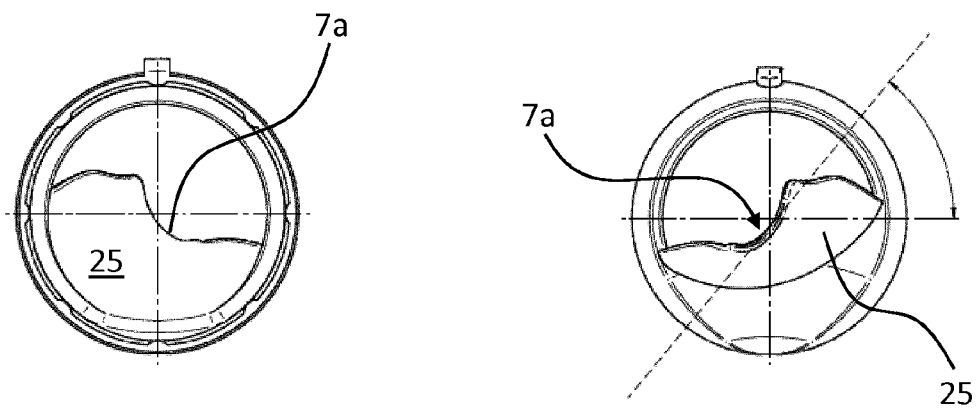
FIG. 12a shows an embodiment of the inventive attachment with asymmetrical guide pane viewed in the lengthwise direction of the attachment.
FIG. 12b shows the attachment from FIG. 12a viewed in the opposite direction.
Figure 13A:
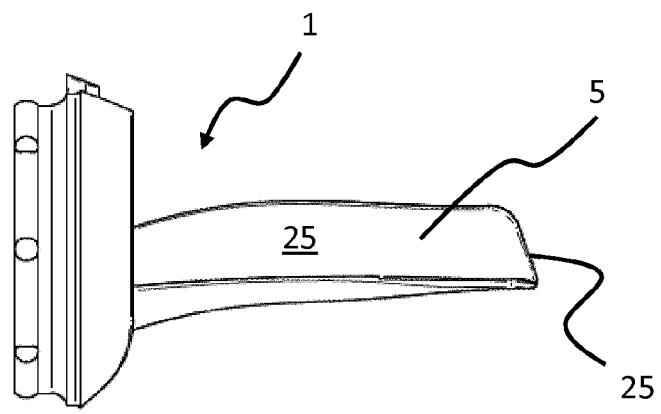
Figure 13B:
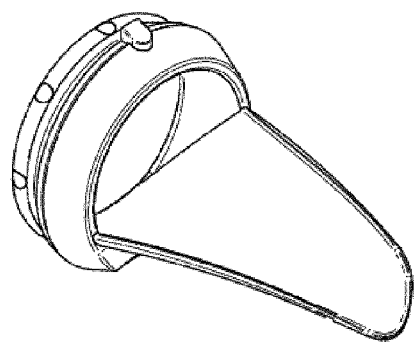
Figure 13C:
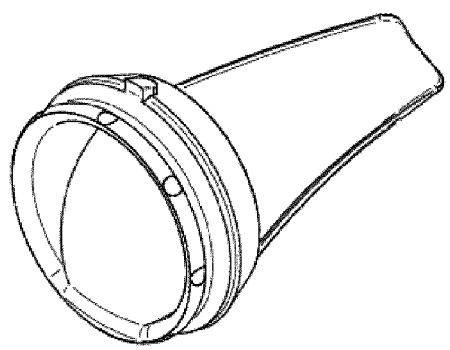

FIGS. 11*a* and 11*b* show a fifth embodiment of the inventive attachment 1. All of the previously made comments concerning the first, second, third and fourth embodiments also apply to the fifth embodiment, illustrated here. In addition, two inflow elements 35 are arranged on the guide pane bottom 25 of the guide pane 5 of the attachment 1.

The inflow elements 35 here each have the shape of a right-angle triangle, as can clearly be seen from FIGS. 11*a* and 11*b*, and are arranged in a central lengthwise portion of the guide pane 5. The inflow elements 35, through the connection pieces 4, set inflow surfaces against the fluid stream flowing into the attachment 1 by way of the connection pieces 3, which inflow surfaces in preferred manner run perpendicular to the streaming direction of the contiguous fluid stream, so that the contiguous streaming of the fluid is disturbed and is forced into an eddy motion; one or more eddies 36 (vortex) of the fluid introduced into the auditory canal are configured. As can clearly be seen from FIG. 11*b*, the inflow elements 35 are arranged on the guide pane bottom 25 in such a way that the inflow elements 35 face one another and the distance between the inflow elements 35 is reduced toward the end 7 of the guide pane 5.

FIG. 12*a*, 12*b*, 13*a*, 13*b* and 13*c* show a sixth embodiment of the inventive attachment (1). All of the statements expressed above in connection with the first, second, third, fourth and fifth embodiment is also applied to the sixth embodiment illustrated here. In addition, the guide pane bottom (25) of this embodiment is not symmetrical, as is the case with the other embodiments described above, but rather asymmetrical.

This can be achieved if portions of the guide pane frames 26, 27 situated opposite one another each are of different height, or if the guide pane bottom 25 is pushed and/or rotated with respect to a first lengthwise portion in the area of a second lengthwise portion of the guide pane bottom 25. In particular, the second portion 5*b* of the guide pane 25 curved in the second direction, as shown, can be rotated with respect to the first portion 5*a* of the guide pane 25.

What is claimed is:

1. An attachment for a device for generating an air flow or dispensing a fluid, which attachment is designed to be at least partially introduced into an external auditory canal of a human or animal ear, the attachment comprising:
    a connection piece for connecting to the device;
    a tongue-type guide vane extending from the connection piece in a streaming direction of the air flow or fluid, for conducting the air flow or fluid out of the device via the connection piece; and
    at least one inflow element that extends beyond a guide vane bottom in order to agitate the air flow or fluid flowing out of the device.

2. The attachment according to claim 1, wherein at least two inflow elements are positioned on the guide vane bottom opposite one another.

3. The attachment according to claim 2, wherein the at least two inflow elements have the shape of a right-angle triangle.

4. The attachment according to claim 2, wherein inflow surfaces of the at least two inflow elements face the connection piece and run perpendicular to one another.

5. The attachment according to claim 1, wherein, when viewed from the connection piece, a distance between opposite-situated inflow elements decreases in a lengthwise direction of the attachment.

6. The attachment according to claim 1, wherein a first portion and a second portion of the guide vane bottom directly connect with one another.

7. The attachment according to claim 1, wherein the attachment includes an ear funnel, which ear funnel encloses the tongue-type guide vane at least partially in a lengthwise direction and includes a proximal opening, with which proximal opening the attachment, according to appropriate use, is introduced into or applied to the external auditory canal, so that the proximal opening constitutes the opening of the ear funnel closest to the eardrum, wherein the ear funnel is connected onto the connection piece and stands apart from it, or the connection piece forms an end portion of the ear funnel.

8. The attachment according to claim 1, wherein, from the viewpoint of a lengthwise section of the attachment, the guide vane bottom intersects a lengthwise axis of the attachment, said lengthwise axis running through the center point of a cross-section of the connection piece standing perpendicular on the lengthwise section.

9. The attachment according to claim 7, wherein, from the viewpoint of a lengthwise section of the attachment, the guide vane bottom intersects a lengthwise axis of the ear funnel, said lengthwise axis running through the center point of the proximal opening of the ear funnel.

10. The attachment according to claim 9, wherein the lengthwise axis of the ear funnel coincides with a lengthwise axis of the attachment.

11. The attachment according to claim 1, wherein the tongue-type guide vane comprises two guide vane frames extending from the guide vane bottom, namely a first guide vane frame and a second guide vane frame, wherein the guide vane bottom and guide vane frames configure a guide duct or part of a guide duct for the air flow or fluid flowing out of the device.

12. The attachment according to claim 11, wherein the first guide vane frame extends from a first lengthwise border of the guide vane bottom and the second guide vane frame extends from a second lengthwise border of the guide vane bottom situated opposite the first lengthwise border.

13. The attachment according to claim 1, wherein the tongue-type guide vane comprises a portion running in the connection piece.

14. The attachment according to claim 7, wherein the tongue-type guide vane is arranged completely within the ear funnel and/or the connection piece.

15. The attachment according to claim 7, wherein the ear funnel tapers in the direction from the connection piece to the proximal opening of the ear funnel.

16. The attachment according to claim 7, wherein a proximal end of the tongue-type guide vane, which proximal end, according to appropriate use, constitutes the end of the tongue-type guide vane closest to the eardrum, is positioned inside the proximal opening of the ear funnel.

17. The attachment according to claim 16, wherein the proximal end of the tongue-type guide vane divides the proximal opening of the ear funnel into an outflowing opening for air flowing out of the attachment into the auditory canal as well as an inflow opening for air flowing out of the auditory canal into the attachment.

18. The attachment according to claim 17, wherein the tongue-type guide vane divides an inner volume of the ear funnel into a ventilation duct for air flowing from the attachment into the auditory canal as well as an exhaust air duct for air flowing out of the auditory canal into the attachment, wherein the ventilation duct connects the connection piece with the exhaust air flow opening and wherein the exhaust air duct connects the inflow opening with an outlet of the attachment.

19. The attachment according to claim 18, wherein a cross-section of the ventilation duct decreases as it extends in the streaming direction.

20. The attachment according to claim 7, wherein an outlet of the attachment is formed by an opening in a housing wall of the ear funnel.

21. The attachment according to claim 7, wherein the connection piece and the tongue-type guide vane are configured as a single unit and can be connected as a unit with the ear funnel, or that the ear funnel and the tongue-type guide vane are configured as a single unit and can be connected as a unit with the connection piece, or that the connection piece, the tongue-type guide vane, and the ear funnel are configured as a single unit.

22. The attachment according to claim 7, wherein the connection piece is constituted by an end portion of the ear funnel.

23. The attachment according to claim 1, wherein the connection piece is designed to connect the attachment twistably on the device.

24. The attachment according to claim 23, wherein the connection piece comprises at least one indentation on an external enclosure surface, which indentation can engage with at least one clasping hook of the device in order to block the attachment in a particular twisting position on the device.

25. The attachment according to claim 24, wherein several indentations are positioned at a distance from one another on the outer enclosing surface of the connection piece in order to be able to block the attachment in different twisting positions on the device.

26. The attachment according to claim 25, wherein the indentations are at an angle to one another of up to 180°.

27. The attachment according to claim 1, wherein the guide vane bottom, at least in an area of a second lengthwise portion of the guide vane, is rotated with respect to a first lengthwise portion of the tongue-type guide vane.

28. The attachment according to claim 11, wherein the first guide vane frame and the second guide vane frame are each of different height.

29. An ear-drying instrument including a device for generating an air flow as well as an attachment according to claim 1.

30. A device for the care or therapeutic treatment of the exterior auditory canal of a human or animal ear including a device for dispensing a fluid as well as an attachment according to claim 1.

* * * * *